United States Patent [19]

Tsukamoto et al.

[11] Patent Number: 4,681,848
[45] Date of Patent: Jul. 21, 1987

[54] NOVEL PEPTIDE AND USE THEREOF

[75] Inventors: Kyozo Tsukamoto, Suita; Yuzo Ichimori, Sakai; Mitsuhiro Wakimasu, Suita, all of Japan

[73] Assignee: Takeda Chemical Industries, Ltd., Osaka, Japan

[21] Appl. No.: 534,091

[22] Filed: Sep. 20, 1983

[30] Foreign Application Priority Data

Sep. 22, 1982 [WO] PCT Int'l Appl. ... PCT/JP82/00381
Nov. 22, 1982 [WO] PCT Int'l Appl. ... PCT/JP82/00444
May 31, 1983 [WO] PCT Int'l Appl. ... PCT/JP83/00174

[51] Int. Cl.$^4$ .............................................. C12N 5/00
[52] U.S. Cl. .................................... 435/240; 435/68; 435/172.2; 435/948; 530/387; 935/89; 935/93; 935/95; 935/102; 935/103; 935/104; 935/105; 935/108; 935/110
[58] Field of Search .................. 435/240, 172.1, 172.2, 435/68; 935/89, 93, 95, 102, 103–105, 108; 260/112 R; 530/387

[56] References Cited

PUBLICATIONS

Oleszak et al., Hybridoma, 2(1983), 439–449.
Novick et al., The Embo Journal, 2(1983), 1527–30.
Nature, 256, 495–499 (1975).
Nature, 285, 446–450 (1980).
European J. of Immunology, 9, 94–96 (1979).
Nature, 286, 110 (1980).
The Interferon System, Springer, 11–26, New York, 1979.
Blood, 55, 711–721 (1980).
Blood, 55, 875–884 (1980).
Biochemica et Biophysica Acta, 516, 231–247 (1978).
Cellular Immunology, 49, 390–394 (1980).
Proc. Natl. Acad. Sci. USA, 79, 1820–1824 (1982).
Nature, 295, 503–508 (1982).
Neucleic Acids Res., 10, 2487–2501 (1982).
Nature, 296, 258–259 (1982).
Science, 144, 1334–1336 (1964).
J. Biochemistry, 79, 223–224 (1976).
Immunopharmacology, 1, 3–12 (1978).
Current Topics in Microbiology and Immunology, 81, 1–7 (1978).
Applied Microbiology, 16, 1706–1707 (1968).
J. Biological Chem., 256, 9750–9754 (1981).
Nature, 227, 680–685 (1970).
Methods in Enzymology, 11, 197–199 (1967).
Eur. J. Biochem., 8, 189–199 (1969).
Altex Chromatogram, 3, 8 (1980).
J. Mol. Biol., 96, 495–509 (1975).
Proc. Natl. Acad. Sci. USA, 75, 5765–5769 (1968).
Nucleic Acids Res., 9, 6103–6114 (1981).
Nucleic Acids Res., 7, 1513–1523 (1979).
J. Mol. Biol. 121, 113–132 (1978).
J. Immunology, 129, 2357–2359 (1982).

*Primary Examiner*—Christine M. Nucker
*Attorney, Agent, or Firm*—David G. Conlin; Gregory D. Williams; Ronald I. Eisenstein

[57] ABSTRACT

The invention relates to novel polypeptide of the formula

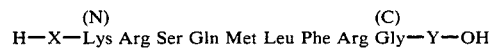

wherein X is a bond, or a peptide or amino acid residue 1 to 16 amino acids counting from the C terminus of the peptide chain of

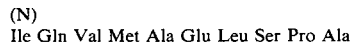

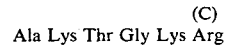

and Y is a peptide or amino acid residue having 1 to 5 amino acids counting from the N terminus of the peptide chain of

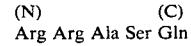

and conjugate between the same and a carrier protein, as well as hydridoma and monoclonal antibody derived by the use of the polypeptide or the conjugate, and a method of detecting and of purifying human gamma-interferon using the antibodies.

9 Claims, 11 Drawing Figures

A   bovine serum albumin
B   ovalbumin
C   carbonic anhydrase
D   trypsin inhibitor (soy bean)
E   lysozyme 1:  molecular weight marker
2:  protein (with 2-mercaptoethanol)
3:  protein (without 2-mercaptoethanol)

relative mobility

A   bovine serum albumin
B   ovalbumin
C   carbonic anhydrase
D   trypsin inhibitor
E   lysozyme

```
                                            S1
5' ACTTCTTTGGCTTAATTCTGTCGGAAACG ATG AAA TAT ACA AGT TAT ATC TTG

S20    1
   GCT TTT CAG CTC TGC ATC GTT TTG GGT TCT CTT GGC TGT TAC TGC CAG

20
   GAC CCA TAT GTA AAA GAA GCA GAA AAC CTT AAG AAA TAT TTT AAT GCA

GGT CAT TCA GAT GTA GCG GAT AAT GGA ACT CTT TTC TTA GGC ATT TTG

40
   AAG AAT TGG AAA CAG CAG AGT GAC AGA AAA ATA ATG CAG AGC CAA ATT

60
   GTC TCC TTT TAC TTC AAA CTT TTT AAA AAC TTT AAA GAT GAC CAG AGC

80
   ATC CAA AAG AGT GTG GAG ACC ATC AAG GAA GAC ATG AAT GTC AAG TTT

100
   TTC AAT AGC AAC AAA AAG AAA CGA GAT GAC TTC GAA AAG CTG ACT AAT

TAT TCG GTA ACT GAC TTG AAT GTC AAA CGC AAA GCA ATA CAT GAA CTC

120
   ATC CAA GTG ATG GCT GAA CTG TCG CCA GCA GCT AAA ACA GGG AAG CGA 140                      146
   AAA AGG AGT CAG ATG CTG TTT CGA GGT CGA AGA GCA TCC CAG TAA TGG
```

TTGTCCTGCCTGCAATATTTGAATTTTAAATCTAAATCTATTTATTAATATTTAACATTATTT
ATATGGGGAATATATTTTTAGACTCATCAATCAAATAAGTATTTATAATAGCAACTTTTGTGT
AATGAAAATGAATATCTATTAATATATGTATTATTTATAATTCCTATATCCTGTGACTGTCTC
ACTTAATCCTTTGTTTTCTGACTAATTAGGCAAGGCTATGTGATTACAAGGCTTTATCTCAGG
GGCCAACTAGGCAGCCAACCTAAGCAAGATCCCATGGGTTGTGTGTTTATTTCACTTGATGAT
ACAATGAACACTTATAAGTGAAGTGATACTATCCAGTTACTGCCGGTTTGAAAATATGCCTGC
AATCTGAGCCAGTGCTTTAATGGCATGTCAGACAGAACTTGAATGTGTCAGGTGACCCTGATG
AAAACATAGCATCTCAGGAGATTTCATGCCTGGTGCTTCCAAATATTGTTGACAACTGTGACT
GTACCCAAATGGAAAGTAACTCATTTGTTAAAATTATCAATATCTAATATATATGAATAAAGT
G 3'

Figure 5

NOVEL PEPTIDE AND USE THEREOF

FIELD OF THE INVENTION

This invention relates to novel polypeptides and use thereof.

BACKGROUND ART

Hybridoma technology for the production of monoclonal antibodies, which was developed by Köhler and Milstein [Nature, 256, 495 (1975)], has recently come into frequent use. This technology has several marked features; for instance, antibodies of a single specificity to each antigenic determinant can be produced, and antibodies obtained against roughly purified specimens need no absorption procedure. Moreover, from the viewpoint of antibody production, the technology is advantageous in many aspects, for instance in that when hybridomas are grown, particularly in mammalian heat high-titer antibody specimens can be obtained as desired, in large amounts and with constant quality and good reproducibility. In this sense, the utility of the technology of obtaining monoclonal antibodies by use of hybridoma is rated high. The modes of utilization of monoclonal antibodies are not limited to antigen detection. For instance, they are used for the purification of trace components through the preparation of antibody columns [Nature, 285, 446 (1980)]. Furthermore, the use thereof as diagnostic reagents or therapeutic agents has been developed [European Journal of Immunology, 9, 94 (1979)].

It is known that human interferon (IEN) includes at least three antigenically different types, namely alpha, beta and gamma [Nature, 286, 110 (1980)]. It is also known that gamma-interferon (IFN-γ) is produced mainly by T lymphocytes receiving stimulation from a mitogen or antigen, and IFN-γ is also called immune interferon (I-IFN) [The Interferon System, Springer Publishing Co., New York, 1979]. It is anticipated that IFN-γ is produced in living bodies as a result of various immune responses, and it is presumed that IFN-γ plays an important role in immuno-regulation. IFN-γ differs in antigenic characteristics and in inducer species from alpha-interferon (IFN-α) and beta-interferon (IFN-β). It is further known that IFN-γ is acid-labile and heat-labile [The Interferon System, Springer Publishing Co., New York, 1979].

IFNs are generally defined as antivirally active substances produced by living bodies. It has been proved that they have various other biological activities, and their antitumor activity is a focus of attention [Blood, 55, 711, (1980); ibid., 55, 875, (1980)]. For inhibiting tumor growth, two methods are conceivable. One is direct inhibition of tumor cell proliferation and the other is indirect inhibition of tumor growth via immune responses in hosts. The latter case possibly includes natural killer (NK) cell activation, macrophage activation and killer T cell activation, among others. In fact, it has been demonstrated that IFNs exert various immune-response-potentiating actions such as mentioned above in addition to direct actions [Biochemica et Biophysica Acta, 516, 231, (1978)]. Since IFN-γ is by far higher in such various in vitro activities associated with antitumor effect and in vivo activities than IFN-α and IFN-β, its importance has been emphasized [Cellular Immunology, 49, 390, (1980)].

However, the IFN-γ-potency that can be induced in vitro is generally low, few established cell lines are adequate enough as IFN-γ-producing ones, and IFN-γ purification is difficult due to its lability to heat and acids. For these and other reasons, the large-scale production and purification of IFN-γ have been much delayed as compared with IFN-α and IFN-β.

Very recently, it was reported that natural IFN-γ could be made singly [Proceedings of the National Academy of Science, 79, 1820, (1982)], but recovery of activity is very poor. A more effective purification method, therefore, has been eagerly waited for.

On the other hand, cloning of the human IFN-γ gene has been reported, as well as production of an approximately 17 kilodalton molecular species composed of 146 amino acids, supposed to be IFN-γ in *Escherichia coli* [Nature, 295, 503, (1982); Nucleic Acids Research, 10, 2487, (1982)]. However, natural product IFN-γ reportedly includes various species having different molecular weights and the counterpart relationship among the molecular species is unknown.

The present inventors have obtained monoclonal antibodies which are able to distinguish various IFN-γ species which is not only important for establishing the correspondency among molecular species but also provides a very powerful weapon for purifying natural IFN-γ or IFN-γ produced in *Escherichia coli* by using genetic engineering techniques. A very recent report describes the acquisition of a monoclonal antibody against natural IFN-γ [Nature, 296, 258, (1982)]. When IFN-γ comprises a plurality of molecular species, it is very important to obtain monoclonal antibodies to molecular species cloned by gene manipulation techniques.

DISCLOSURE OF THE INVENTION

Based on the reported amino acid sequence of human IFN-γ reduced from the nucleotide sequence of its structural gene [Nucleic Acids Research, 10, 2487 (1982)], the present inventors synthesized, chemically a C-terminal polypeptide taken from said amino acid sequence, namely peptide of the formula

wherein X is a bond, or a peptide or amino acid residue having 1 to 16 amino acids counting from the C terminus of the peptide chain of

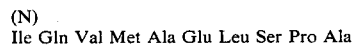

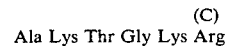

and Y is a peptide or amino acid residue having 1 to 5 amino acids counting from the N terminus of the peptide chain of

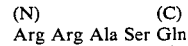

and furthermore the present inventors produced protein conjugate suitable for raising antibodies, by coupling chemically the above peptide chemically with a carrier protein.

The thus-obtained polypeptide and protein conjugate were used for immunization of mammals, and hybridomas were made by cell fusion of spleen cells taken from the mammals with lymphoid cells from the same or different species of mammals and cloned.

Inoculating the thus-obtained hybridomas into mammal, allowing them to grow and produce monoclonal antibodies, and recovering the ascites gave monoclonal antibodies against the above-mentioned polypeptide.

Furthermore, the present inventors established a method of purifying human IFN-γ from a crude product containing human IFN-γ using the monoclonal antibodies obtained and also a method of detecting human IFN-γ by radioimmunoassay (RIA) or enzyme immunoassay (EIA) using the same.

Thus, the present invention provides novel polypeptide (I), protein conjugate thereof, novel cloned hybridoma, novel monoclonal antibody, and methods of production thereof, and further the use of said monoclonal antibody, e.g. for purification or analysis.

Referring to the above polypeptide (I), it is preferable that Y is Arg Arg Ala Ser Gln or/and X is Lys Arg. Furthermore, it is preferable that the polypeptide (I) contains 15 to 25 amino acid residues.

Said peptide can be produced by the conventional methods of peptide synthesis. Any of the solid phase methods and the liquid phase methods may be used, although the liquid phase synthetic method is advantageous in many cases. Such methods of peptide systhesis are described, for example, by Schröder and Lubke in "The Peptides", vol. 1, Academic Press, New York, U.S.A., 1966, or by Izumiya et al. in "Peptide Syntheses", Maruzen, Tokyo, Japan, 1975, or by Haruaki Yajima in "Experiments in Biochemistry, vol. 1, pages 207–400", Tokyo Kagaku Dojin, 1977, and include, among others, the azide method, chloride method, acid anhydride method, mixed acid anhydride method, DCC method, active ester method, method using Woodward reagent K, carbodiimidazole method, oxidation/reduction method and DCC/additive (e.g. HONB, HOBt, HOSu) method.

Said peptide can be produced by condensing (a) a reactive carboxyl-containing starting material corresponding to a partial component of polypeptide (I) with (b) a reactive amino-containing starting material corresponding to the remainder of polypeptide (I), both being optionally protected by any of the conventional peptide synthesis methods and, in case the condensation product has a protective group, eliminating the protective group in the conventional manner.

The method of protecting a functional group which should not be involved in the reaction between the materials, the protective group to be used in such protection, the method of eliminating such protective group and the method of activating the functional group to be involved in the reaction, for instance, can be selected adequately from among known ones or means.

Thus, the protective group for the amino group in the starting material includes, among others, carbobenzoxy, t-butyloxycarbonyl, t-amyloxycarbonyl, isobornyloxycarbonyl p-methoxybenzyloxycarbonyl, 2-chlorobenzyloxycarbonyl, adamantyloxycarbonyl, trifluoroacetyl, phthalyl, formyl, o-nitrophenylsulfenyl, diphenylphosphinothioyl and 4-methoxy-2,3,6-trimethylbenzenesulfonyl. The carboxyl-protecting group includes alkyl ester groups (e.g. esterforming groups such as methyl, ethyl, propyl, butyl and t-butyl), benzyl ester group, p-nitrobenzyl ester group, p-methoxybenzyl ester group, p-chlorobenzyl ester group, benzhydryl ester group, carbobenzoxyhydrazide group, t-butyloxycarbonylhydrazide group and tritylhydrazide group, among others.

The protective group for the guanidino group of arginine is, for example, nitro, tosyl, p-methoxybenzenesulfonyl, carbobenzoxy, isobornyloxycarbonyl, admantyloxycarbonyl, 4-methoxy-2,6-dimethylbenzenesulfonyl or pentamethylbenzenesulfonyl. The guanidino group may also be protected in the form of an acid (e.g. benzenesulfonic, toluenesulfonic, hydrochloric or sulfuric acid) salt.

The hydroxyl group of threonine and serine can be protected by esterification or etherification, for instance. Groups adequate for this esterification are, for example, lower alkanoyl groups, such as acetyl, aroyl groups, such as benzoyl, and carbonic acid-derived groups, such as benzyloxycarbonyl and ethyloxycarbonyl. Groups suited for the etherification are, for instance, benzyl, tetrahydropyranyl and t-butyl. However, the hydroxyl group of threonine does not always need protection. Methionine may be protected in the form of a sulfoxide. The activated form of carboxyl in the starting material includes, among others, the corresponding acid anhydrides, azides and active esters (esters with pentachlorophenol, p-nitrophenol, N-hydroxysuccinimide, N-hydroxybenzotriazole, N-hydroxy-5-norbornene-2,3-dicarboximide, etc.). In some cases, the peptide bond-forming reaction can be carried out in the presence of a dehydrating agent (e.g. dicyclohexylcarbodiimide, carbodiimidazole or the like carbodiimide reagent).

The peptide condensation reaction can be conducted in the presence of a solvent. The solvent may be selected adequately from among those known to be usable in the peptide condensation reaction. Examples are anhydrous or aqueous dimethylformamide, dimethyl sulfoxide, pyridine, chloroform, dioxane, dichloromethane, tetrahydrofuran, ethyl acetate and N-methylpyrrolidone, and adequate mixtures of these.

The reaction temperature is selected within the range known to be usable in the peptide bond-forming reaction, generally within the range of about −40° C. to about 60° C., preferably within the range of about −20° C. to about 0° C.

After completion of the condensation reaction, the protective group, if present in the product, can be eliminated by the conventional method, for instance the reductive method (e.g. hydrogenation using a catalyst such as palladium black, reduction with metallic sodium in liquid ammonia) or acidolysis (e.g. acidolysis with trifluoroacetic acid, hydrogen fluoride or methanesulfonic acid or a mixture thereof either in the absence of presence of a sulfur-containing compound such as thioanisole).

The peptide of the present invention as produced in the above manner can be recovered from the reaction mixture after completion of the reaction by ordinary means of separating peptides, such as extraction, partition and/or column chromatography.

Referring to the conjugate between polypeptide (I) and a carrier protein, the kind of carrier protein and the ratio of carrier to hapten (in the present case, the polypeptide) are optional, provided that an antibody can be produced in an efficient manner against the hapten coupled with the carrier for immunization. Bovine serum albumin bovine thyloglobulin, hemocyanin or poly-L-lysine, for instance, may be used for coupling in an amount of 0.1–20, preferably 1–5 parts by weight per part by weight of the hapten.

For the coupling of the hapten with a carrier, a variety of condensing agents may be used. The use of glutaraldehyde or a carbodiimide is preferable.

Mammals usable in immunization with the polypeptide (I) or protein conjugate thereof are experimental animals such as sheep, goats, rabbits, guinea pigs, rats and mice. For the production of monoclonal antibodies, rats and mice are preferred. The immunization of mice, for instance, can be carried out by any of the subcutaneous, intraperitoneal, intravenous, intramuscular, intradermal and other routes and, in many cases, subcutaneous, intraperitoneal or intravenous (especially subcutaneous) infusion is preferable. The immunization interval and immunizing dose, among others, may vary over a wide range, and various modifications are possible. For instance, the immunization may be repeated 2 to 6 times at a 2-week interval, and spleen cells excised 1–5 days, preferably 2–4 days, after the last immunization. In each immunization, the immunizing dose of the peptide is desirably not less than 0.1 $\mu$g, peferably 10–300 $\mu$g. It is also desirable to make partial blood sampling prior to spleen excision and perform cell fusion experiments using spleen cells after confirmation of an increased blood antibody level.

As to the above-mentioned cell fusion of spleen cells with lymphoid cells, the lymphoid cell is that from a mammal of the same or different species from the immunized mammal (preferably the same species), and cell fusion is carried out, for instance, between excised mouse spleen cells and a lymphoid cell line, such as myeloma cell line having a marker such as hypoxanthine-guanine-phosphoribosyl transferase deficiency (HGRRT$^-$) or thymidine kinase deficiency (TK$^-$). For the fusion, a fusing agent, such as Sendai virus or polyethylene glycol (PEG), is used. It is of course possible to add a fusion accelerator such as dimethyl sulfoxide (DMSO). The degree of polymerization of PEG is generally 1000–6000, the treatment period is 0.5–30 minutes, and the concentration is 10%–80%, for instance. In a preferred example, the fusion can be effected efficiently by treatment with PEG 6000 at 35–55% for 4–10 minutes. The fused cells can be selectively grown using a hypoxanthine-aminopterine-thymidine medium [HAT medium; Nature, 256, 495, (1975)], for instance.

The culture supernatant obtained after cell growth can be screened for the production of the desired antibody. The screening for antibody titer can be made in the following manner. Thus, in the first step, the production or nonproduction of an antibody against the peptide used for immunization can be checked by an appropriate method, such as RIA or EIA. Various modifications are possible for such method. As a preferred method of measurement, mention is made of a method using EIA. Rabbit anti-mouse immunoglobulin antibody, for instance, is coupled with a carrier, such as cellulose in bead form, by the conventional method. The culture supernatant to be tested or mouse serum is added, and the reaction is allowed to proceed at a constant temperature (which hereinafter means 4°–40° C.) for a predetermined period of time. The reaction product is washed well, then an enzyme-labelled peptide (prepared by coupling the peptide with an enzyme by the conventional method followed by purification) is added, and the reaction is allowed to proceed at a constant temperature for a predetermined period of time. The reaction product is washed well, an enzyme substrate is added, and the reaction is allowed to proceed at a constant temperature for a predetermined period. Thereafter, the resulting colored product can be assayed through the intensity of absorption or fluorescence, for instance.

The cells in a well, after growth in a selective medium and detection of antibody activity against the peptide used for immunization, are desirably cloned by the limiting dilution method, for instance. The cloned cell culture supernatant is screened in the same manner, and the cells in a well having a high anitbody titer are grown. In this manner, a monoclonal antibody-producing hybridoma clone which is responsive to the peptide used for immunization can be obtained.

In the next place, it is necessary to examine whether the antibody produced by such clone is reactive not only with the peptide used for immunization but also with the very IFN-$\gamma$ molecule. For this purpose, methods are available, for example a method which examines the reactivity by RIA or by EIA using radio- or enzyme-labelled IFN-$\gamma$ and a method which examines whether the biological activity (IFN-$\gamma$ activity) is absorbed by the antibody. The latter is advantageous in that purification of IFN-$\gamma$ is not required. An advantageous example is described in the below, but other methods may also be used, for instance a method comprising removing an immune precipitate using protein A and assaying the remaining IFN-$\gamma$ activity in the supernatant. In said example, rabbit anti-mouse immunoglobulin antibody, for instance, may be coupled with a carrier such as cellulose in bead form by the conventional method, the hybridoma supernatant to be assayed or mouse serum is added, and the reaction is allowed to proceed at a constant temperature for a predetermined period. The reaction product is washed well, and a known quantity of IFN-$\gamma$ is added. As the IFN-$\gamma$, there may be used, for instance, a culture supernatant containing IFN-$\gamma$ induced from human peripheral blood lymphocytes with lectin and a phorbol ester, an extract containing recombinant IFN-$\gamma$ produced by E. coli etc. or the like. After the addition of IFN-$\gamma$, the reaction is allowed to proceed at a constant temperature for a predetermined period and then the remaining IFN-$\gamma$ activity in the supernatant is measured. In this manner, the absorption of IFN-$\gamma$ activity by the antibody can be determined.

The thus-cloned hybridoma is grown in a liquid medium or in peritoneal cavity of a mammal to produce the monoclonal antibody of the present invention.

The hybridoma is cultured, for instance, in a liquid medium, such as RPMI-1640 with 0.1–40% bovine serum added, for 2–10 days, preferably for 3–5 days, and said monoclonal antibody can be obtained from the culture broth. Furthermore, an antibody much higher in titer than the cell culture supernatant can be obtained in a large amount and in an efficient manner by inoculating an adequate mammal, such as the mouse, with the hybridoma intraperitoneally, growing the cells and collecting the ascitic fluid. For this purpose, mice, such as BALB/c mice, preinoculated with mineral oil or the like may be intraperitoneally inoculated with $1 \times 10^4$ to $1 \times 10^7$ cells, preferably $5 \times 10^5$ to $2 \times 10^6$ cells, of the hybridoma and, after 7–20 days, preferably after 10–14 days, the ascitic fluid or the like is collected. The antibody formed and accumulated in the ascitic fluid can be isolated easily by fractionation with ammonium sulfate and DEAE-cellulose column chromatography, for instance, to give a monoclonal antibody in the form of a pure immunoglobulin.

The monoclonal antibody in accordance with the present invention has the following characteristic features:

(1) It binds to the polypeptide (I) used for immunization;
(2) It binds to the IFN-γ molecule but not to IFN-α or IFN-β;
(3) It belongs to the antibody subclass IgG$_2$b or IgG$_1$ when tested by the Ouchterlony method;
(4) In SDS-polyacrylamide gel electrophoresis, it gives only two bands exactly corresponding to the H and L chains of a standard immunoglobulin.

The monoclonal antibody can be safely produced, used and stored.

The monoclonal antibody obtained in accordance with the present invention can be used for the detection of a trace amount of IFN-γ in vivo or in vitro by making use of an EIA or RIA method and moreover can be used in purifying very efficiently IFN-γ, which is either natural or made by gene manipulation, by preparing antibody columns, for instance, though the purification of IFN-γ has been considered very difficult.

For instance, for the detection of IFN-γ, an IFN-γ-containing sample or a standard IFN-γ sample is subjected to reaction with said monoclonal antibody labelled, for example, with radioactive iodine or an enzyme, then protein A, for instance, is added so as to cause immune complex precipitation and, after an adequate period of reaction, the radioactivity or enzyme activity in the precipitated immune complex is determined. In this manner, an IFN-γ assay can be performed in a simple and easy way.

One example of IFN-γ assay by competitive method is as following. IFN-γ can be assayed by labelling the polypeotide (I), for instance, with radioactive iodine or an enzyme, allowing a sample containing IFN-γ to be assayed to coexist in the system of reaction of the labelled polypeptide (I) with a definite amount of the unlabelled monoclonal antibody of this invention, and causing the resulting immune complex to precipitate or be bound to an anti-mouse antibody. Purified IFN-γ may be used as the radioactive iodine- or enzyme-labelled material in place of the polypeptide (I) [Science, 158, 1570 (1968); Immunochemistry, 15, 429 (1971)]

Another example of IFN-γ assay by competitive method is as following. Partially purified IFN-γ or the polypeptide (I), for instance, is immobilized on a microtray or the like solid phase. Immobilization can be effected, for example, by suspending IFN-γ or the polypeptide (I) in phosphate buffer containing 0.1M sodium bicarbonate in a concentration of 0.1 to 100 μg/ml, preferably 10 to 20 μg/ml, and placing 100 μl of the suspension in each well on a microtray, followed by leaving for 24 hours. IFN-γ can be assayed by adding to said well the product obtained by reacting the monoclonal antibody of this invention with a sample containing IFN-γ to be assayed at 37° C. for an hour or at 4° C. for 20 hours, and further adding a radioactive iodine- or enzyme-labelled rabbit anti-mouse antibody or the like. When an enzyme-labelled rabbit anti-mouse antibody or the like is used in such series of EIA methods, rapid assay becomes possible through the use of a photometer such as Multiskan (Flow Lab.) or the like photometer in the so-called ELISA (enzyme linked immunosorbent assay) method. Furthermore, the use of monoclonal antibodies produced by two hybridoma clones differing in the antigen recognition site may enable more simplified IFN-γ assay by the so-called sandwich method [Eur. J. Biochem., 71, 459(1976)]. If an antigen adequate for the IFN-γ assay using such EIA or RIA methods is obtained, various modifications are of course possible, and therefore the methods mentioned hereinabove are no more than examples.

For the purification of IFN-γ, said antibody, after purification thereof, is coupled with an appropriate carrier, such as activated agarose gel in the form of beads, by the conventional method, a column is packed with the carrier, and a crude IFN-γ-containing material, such as a culture supernatant or cell lysis product, is applied on the column, whereby IFN-γ is adsorbed thereon. Washing and subsequent elution, for example, with a chaotropic reagent such as KSCN or under weakly acidic conditions which do not lead to inactivation of IFN-γ can give efficiently purified IFN-γ.

The antibody column described above can be prepared, for instance in the following manner, by coupling the monoclonal antibody of the present invention as obtained in the purified state from the ascitic fluid or the like inoculated with the hybridoma with an appropriate carrier.

The carrier may be of any kind provided that, after coupling, IFN-γ can be adsorbed specifically and efficiently and thereafter can be eluted by an adequate means. As an example, agarose gel in the form of beads, which is activated so as to facilitate the bonding of the primary amino group of a protein, for instance AFFI-GEL 10 (Bio-Rad Lab., U.S.A.) can be favorably used in the following manner. The reaction of AFFI-GEL 10 with the antibody is carried out in a buffer solution, such as 0.001-1M, preferably 0.1M, bicarbonate. Usable reaction conditions are 0°-20° C., 10 minutes to 24 hours, and varying pH, and preferred conditions are 4° C., 4 hours and pH 3-10. Th quantitative ratio between AFFI-GEL 10 and the antibody may be selected within the range of up to about 50 mg of antibody per ml of AFFI-GEL, since, in this range, the amount of antibody coupled with AFFI-GEL increases as the amount of antibody increases. From view points of the coupling efficiency and the purification efficiency in the affinity chromatography, the antibody is used in an amount of between 1 mg and 30 mg per ml of AFFI-GEL. The thus-produced antibody-carrier coupling product is washed well with the same buffer solution as used for the reaction and then allowed to stand for several days or treated with ethanolamine hydrochloride in a final concentration of 0.05M at 4° C. for an hour or by some other method so as to block the remaining unreacted active groups, and packed in an appropriate column to give an antibody column.

For the purpose of purification with the above antibody column, a human immune interferon protein-containing sample, for instance, is dissolved in an almost neutral buffer, such as a phosphate buffer or Tris hydrochloride buffer, and made adsorbed on the antibody column. The column is washed with the same buffer and then IFN-γ is eluted. Usable eluents are, for example, a weakly acidic solution (e.g. acetic acid solution), a polyethylene glycol-containing solution, a solution containing a peptide having a higher affinity for the antibody as compared with the sample, a high concentration salt solution, and a combination of these, among others. Those eluents which do not promote decomposition of human IFN-γ to a considerable extent are preferred.

The eluate from the column is neutralized with a buffer by the conventional method. If necessary, the purification procedure using the above antibody column can be repeated.

The thus-obtained human IFN-γ protein solution is dialyzed and, as necessary, can be made into a powder by lyophilization. In carrying out the lyophilization, a stabilizer, such as sorbitol, mannitol, dextrose, maltose or glycerol, can be added.

The thus-obtained human immune interferon protein, when assayed for antiviral activity in a test for evaluating the effect of inhibiting degeneration of human amnion-derived WISH cells by the vesicular stomatitis virus (VSV), shows a specific activity of not less than $10^7$ U/mg.

The IFN activity in U/ml (units/ml) was determined in the following manner. An international standard IFN-α for which the unit has been established and leukocyte-derived crude IFN-γ were assayed in the test for estimating the inhibitory effect against cell degeneration caused in a human amnion-derived FL cell line by VSV, the titer of the lymphocyte-derived IFN-γ was determined by comparison of the titers found, and said IFN-γ was used as a laboratory standard IFN-γ. In calculating the titer of IFN-γ in a material, this laboratory standard IFN-γ was always used in parallel in the above-mentioned assay in the WISH-VSV system and the titer calculation was performed based on the titer ratio.

The human immune interferon protein purified in accordance with the present invention comprises, for instance, a polypeptide having the amino acid sequence of the formula (N)H—A—$Z_1$ Tyr $Z_2$ Gln Asp Pro Tyr Val Lys Glu  (II)
Ala Glu Asn Leu Lys Lys Tyr Phe Asn Ala Gly His
Ser Asp Val Ala Asp Asn Gly Thr Leu Phe Leu Gly
Ile Leu Lys Asn Trp Lys Glu Glu Ser Asp Arg Lys
Ile Met Gln Ser Gln Ile Val Ser Phe Tyr Phe Lys
Leu Phe Lys Asn Phe Lys Asp Asp Gln Ser Ile Gln
Lys Ser Val Glu Thr Ile Lys Glu Asp Met Asn Val
Lys Phe Phe Asn Ser Asn Lys Lys Lys Arg Asp Asp
Phe Glu Lys Leu Thr Asn Tyr Ser Val Thr Asp Leu
Asn Val Gln Arg Lys Ala Ile His Glu Leu Ile Gln
Val Met Ala Glu Leu Ser Pro Ala Ala Lys Thr Gly
Lys Arg Lys Arg Ser Gln Met Leu Phe Arg Gly Arg
Arg Ala Ser Gln—OH(C)

wherein A is Met or a bond, and $Z_1$ and $Z_2$ each is Cys or ½ Cys. The purification procedures according to the present invention can give said polypeptide in a purity of not less than 90%, in particular not less than 95%, on the dried basis.

A human immune interferon protein can be obtained by the purification method according to the present invention.
(1) It exhibits a molecular weight of 17,000±1,000 in SDS-polyacrylamide gel (17.5%) electrophoresis;
(2) It contains cysteine or half cystine or methionine as the amino-terminal amino acid;
(3) It binds to a monoclonal antibody against H-Lys-Arg-Lys-Arg-Ser-Gln-Met-Leu-Phe-Arg-Gly-Arg-Arg-Ala-Ser-Gln-OH.

The human interferon protein purified in accordance with the present invention can be used for the same purposes in the same manner as I-IFN species obtained by the conventional methods. Owing to its smaller contents in contaminant proteins and pyrogen, it can be used more safely as a substance for preparing injections, for instance.

The human I-IFN protein produced by the method of the present invention has antiviral, antitumor, cell proliferation-inhibiting and immunopotentiating activities. The human I-IFN protein produced by the method of the present invention can be mixed with sterilized water, human serum albumin (HSA), physiological saline and other known physiologically acceptable carriers, and can be administered parenterally or locally. For instance, it can be administered intravenously or intramuscularly or by some other route in a dose of 100,000–100,000,000 units, preferably 50,000,000–60,000,000 units, per human adult per day.

The preparations containing the human I-IFN protein of the present invention may also contain other physiologically acceptable inert components such as salt, diluent, adjuvant, another carrier, buffer, binding agent, surfactant and preservative. For parenteral administration, the preparations are provided in the form of a suspension in a sterilized aqueous solution or a physiologically acceptable solvent in ampules or in the form of a sterilized powder (generally obtainable by lyophilization of an I-IFN solution) can be diluted with a diluent prior to use.

Furthermore, the above-mentioned human immune interferon protein-containing preparations may further contain other active ingredients such as IFN-α or IFN-β or a lymphokine (e.g. interleukin 2) in an amount of 1–99% based on the substance of the present invention.

Throughout the specification, the amino acids, peptides, protective groups, active groups and so on, when abbreviated, are abbreviated according to the IUPAC-IUB (Commission on Biological Nomenclature) or the practice in the fields concerned. The following are examples. In case optical isomerism is involved, the amino acids and so on are in the L form unless otherwise specifically indicated.

DNA: Deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecylsulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline Asn: Asparagine
Gln: Glutamine
Z: Carbobenzoxy
Boc: t-Butoxycarbonyl
Mtr: 4-Methoxy-2,3,6-trimethylbenzenesulfonyl
Pme: Pentamethylbenzenesulfonyl
OBu: t-Butyl ester
ONB: N-Hydroxy-5-norbornene-2,3-dicarboxiimide ester
DCC: N,N'-Dicyclohexylcarbodiimide
DCU: N,N'-Dicyclohexylurea
HONB: N-Hydroxy-5-norbornene-2,3-dicarboxiimide
HOBt: N-Hydroxybenzotriazole
CHA: Cyclohexylamine
DCHA: Dicyclohexylamine
TEA: Triethylamine
TFA: Trifluoroacetic acid
MSA: Methanesulfonic acid
THF: Tetrahydrofuran
DMF: Dimethylformamide
MeOH: Methanol
AcOEt: Ethyl acetate

BRIEF DESCRIPTION OF THE DRAWINGS

FIG. 15 illustrates the primary structure (base sequence) of the plasmid pHIT3709 obtained in Reference Example 1 (vii)

Figure 1:
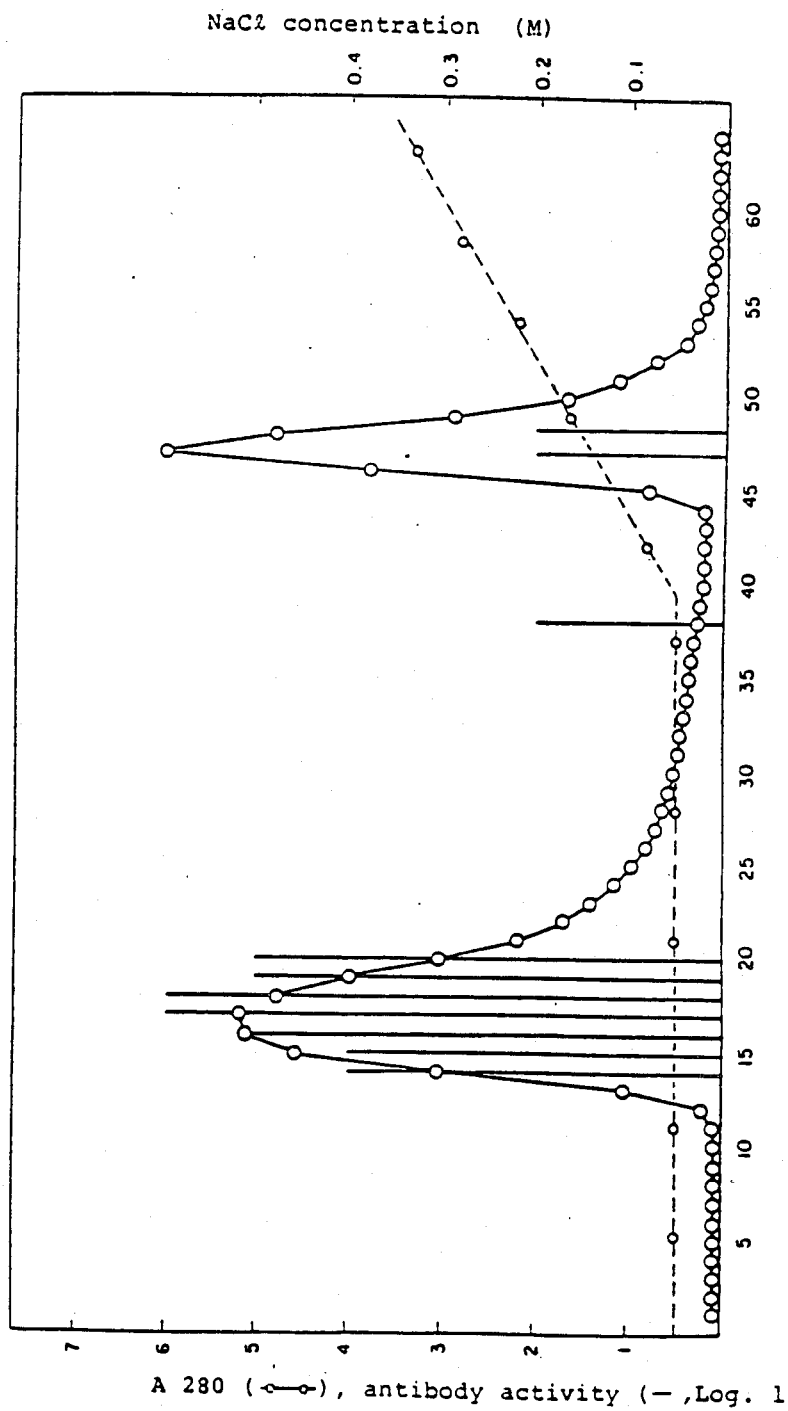
FIG. 1 shows the elution pattern for the monoclonal antibody of the present invention in the DEAE cellulose column in Example 10.

The present invention will be further explained by way of the following working and reference examples, but these examples should be understood not to limit thereby the present invention.

In the following examples, thin layer chromatography was performed using Merck 60F$_{254}$ silica gel plates or Funakoshi Yakuhin's AVICEL SF cellulose plates, with the developing solvents mentioned below:

Rf$^1$: Chloroform-methanol-acetic acid=9:1:0.5
Rf$^2$: Ethyl acetate-pyridine-acetic acid-water=30:10:3:5
Rf$^3$: Chloroform-methanol-water=7:3:0.5
Rf$^4$: n-Butanol-pyridine-acetic acid-water=30:20:6:24
Rf$^5$: Ethyl acetate-n-butanol:acetic acid-water=1:1:1:1

Mouse B hybridomas β2-11.1 (ATCC-HB8699) and γ3-11.1 (ATCC-HB8700) disclosed in the following examples are deposited also at C.N.C.M. of Institut Pasteur, Paris, France under the respective accession No. I-242 and NO. I-243.

EXAMPLE 1

Synthesis of polypeptide corresponding to amino acids 131-136 of γ-IFN (i) Production of Z-Ser-Gln-OBu$^5$ Z-Gln-PBu$^t$ (10.1 g) was dissolved in 500 ml of methanol and catalytic reduction was carried out in a hydrogen gas stream using palladium black as the catalyst. The catalyst was filtered off and the solvent was distilled off. The residue was dissolved together with 7.5 g of Z-Ser-OH and 6.8 g of HONB in 250 ml of DMF and the solution was cooled with ice. DCC (7.15 g) was added with ice-cooling and the mixture was stirred at 0° C. for 4 hours and at room temperature for 12 hours. The formed DCU was filtered off and the solvent was distilled off. The residue was extracted with 300 ml of AcOEt and the extract was washed with 4% aqueous NaHCO$_3$, 0.2N hydrochloric acid and water in that order and dried over anhydrous sodium sulfate. The solvent was then distilled off and the resulting crystalline precipitate was collected by filtration, dried and recrystallized from CH$_3$CN. Yield 6.5 g (51.2%), mp 97°-100° C., $[\alpha]_D^{25}$ −24.1° (c=0.40, methanol) Rf$^1$ 0.64.

Elemental analysis: Calcd. for C$_{20}$H$_{29}$O$_7$N$_3$: C, 56.72; H, 6.90; N, 9.92; Found: C, 56.21; H, 6.72; N, 9.76

(ii) Production of Z-Ala-Ser-Gln-OBu

Z-Ger-Gln-OBu$^t$ (4.23 g) was dissolved in 300 ml of methanol and catalytic reduction was carried out in a hydrogen gas stream using palladium black as the catalyst. The catalyst was filtered off and the solvent was distilled off. The residue was dissolved together with 2.34 g of Z-Ala-OH and 2.27 g of HONB in a mixed solvent composed of 200 ml of EcOEt, 200 ml of dioxane and 100 ml of DMF and the solution was cooled with ice. DCC (2.38 g) was added with cooling and the mixture was stirred at 0° C. for 4 hours and at room temperature for 12 hours. The DCU was filtered off and the solvent was distilled off. CN$_3$CN and ether were added to the residue and the resulting crystalline precipitate was collected by filtration, dried and recrystallized from CH$_3$CN. Yield 3.72 g (75.3%), mp 165°-170° C., $[\alpha]_D^{25}$ −41.2° (c=0.50, methanol) Rf$^1$ 0.60.

Elemental analysis: Calcd. for C$_{23}$H$_{34}$O$_8$N$_4$: C, 55.86; H, 6.93; N, 11.33; Found: C, 55.58; H, 6.74; N, 11.12

(iii) Production of Z-Arg(Pme)-Ala-Ser-Gln-OBu$^t$

Z-Ala-Ser-Gln-OBu$^t$ (3.46g) was dissolved in 300 ml of methanol and catalytic reduction was carried out in a hydrogen gas stream using palladium black as the catalyst. The catalyst was filtered off and the solvent was distilled off. The residue was dissolved in 150 ml of DMF together with Z-Arg(Pme)-OH [prepared from 4.54 g of Z-Arg(Pme)-OH.CHA] and 1.9 g of HOBt, and the solution was cooled with ice. DCC (1.9 g) was added and the mixture was stirred at 0° C. for 4 hours and at room temperature for 15 hours. The DCU was filtered off and the solvent was distilled off. AcOEt was added to the residue and the resulting precipitate was collected by filtration, dried and reprecipitated from methanol and AcOEt. Yield 4.55 g (75.5%), mp 130°–134° C., $[\alpha]_D^{25} -24.1°$ (c=0.26, methanol) $Rf^1$ 0.57.

Elemental analysis: Calcd. for $C_{40}H_{60}O_{11}N_8S\cdot\frac{1}{2}H_2O$: C, 55.22; H, 7.07; N, 12.88; S, 3.69; Found: C, 55.23; H, 6.93; N, 12.54; S, 3.48

(iv) Production of Z-Arg(Pme)-Arg(Pme)-Ala-Ser-Gln-OBu$^t$

Z-Arg(Pme)-Ala-Ser-Gln-OBu$^t$ (4.3 g) was dissolved in 400 ml of methanol and catalytic reduction was carried out in a hydrogen gas stream using palladium black as the catalyst. The catalyst was filtered off and the solvent was distilled off. The residue was dissolved in 200 ml of DMF together with Z-Arg(Pme)-OH [prepared from 3.24 g of Z-Arg(Pme)-OH.CHA] and 1.42 g of HOBt and the solution was cooled with ice. DCC (1.41 g) was added and the mixture was stirred at 0° C. for 4 hours and at room temperature for 20 hours. The DCU was filtered off and the solvent was distilled off. AcOEt was added to the residue and the resulting precipitate was collected by filtration, dried and reprecipitated from methanol and AcOEt. Yield 4.4 g (71.7%), mp 125°–130° C., $[\alpha]_D^{25} -18.0°$ (c=0.40, methanol) $Rf^1$ 0.63.

Elemental analysis: Calcd. for $C_{57}H_{86}O_{14}N_{12}S_2\cdot H_2O$ C, 54.96; H, 7.12; N, 13.50; S, 5.15; Found: C, 54.66; H, 6.92; N, 13.32; S, 5.34

(v) Production of Z-Arg(Pme)-Gly-OBu$^t$

Z-Gly-OBu$^t$ (13.0 g) was dissolved in 500 ml of MeOH and catalytic reduction was carried out in a hydrogen gas stream using palladium black as the catalyst. The catalyst was filtered off and the filtrate was concentrated under reduced pressure. The residue was dissolved in 200 ml of DMF, and Z-Arg(Pme)-OH [prepared from 20.0 g of Z-Arg(Pme)-OH.CHA] and 5.4 g of HOBt were added, followed by ice-cooling. DCC (8.2 g) was added and the mixture was stirred for 48 hours. The formed DCU was filtered off and the filtrate was concentrated. The residue was dissolved in 500 ml of AcOEt and the AcOEt solution was washed with 4% aqueous NaHCO$_3$ and 10% aqueous citric acid, dried over Na$_2$SO$_4$ and concentrated. Petroleum ether was added and the precipitate was collected by filtration. Yield 19.8 (96.8%), mp 71°–73° C., $[\alpha]_D^{23} +0.2°$ (c=0.9, DMF), $Rf^1$ 0.62.

Elemental analysis: Calcd. for $C_{31}H_{45}O_7N_5S$: C, 58.93; H, 7.18; N, 11.09; S, 5.08; Found: C, 59.42; H, 7.58; N, 10.95; S, 4.84

(vi) Production of Z-Phe-Arg(Phe)-Gly-OBu$^t$

Z-Arg(Pme)-Gly-OBu$^t$ (10.0 g) was dissolved in 500 ml of MeOH and catalytic reduction was carried out. The product was then dissolved in 300 ml of DMF. Z-Phe-OH (4.72 g) and 2.35 g of HOBt were added and the mixture was cooled with ice. DCC (3.59 g) was added and the whole mixture was stirred for 15 hours. The formed DCU was filtered off and the filtrate was concentrated. The residue was dissolved in 400 ml of AcOEt and the AcOEt solution was washed with 4% aqueous NaHCO$_3$ and 10% aqueous citric acid, dried over Na$_2$SO$_4$ and concentrated. Ether was added and the resulting crystalline precipitate was collected by filtration and recrystallized from MeOH-ether. Yield 10.5 g (85.3%), mp 101°–103° C., $[\alpha]_D^{26} -8.3°$ (c=0.9, DMF), $Rf^1$ 0.64.

Elemental analysis: Calcd. for $C_{40}H_{54}O_8N_6S$: C, 61.67; H, 6.99; N, 10.79; S, 4.12; Found: C, 61.66; H, 6.56; N, 10.93; S, 4.14

(vii) Production of Z-Leu-Phe-Arg(Pme)-Gly-OBu$^t$

Z-Phe-Arg(Pme)-Gly-OBu$^t$ (5.5 g) was catalytically reduced in 300 ml of MeOH and then dissolved in 300 ml of DMF. Z-Leu-OH (prepared from 3.31 g of Z-Leu-OH.DCHA) and 1.47 g of HONB were added and the mixture was cooled with ice. DCC (1.68 g) was added and the whole mixture was stirred for 48 hours. The formed DCU was filtered off and the filtrate was concentrated. The residue was dissolved in 300 ml of AcOEt and the AcOEt solution was washed with 4% aqueous NaHCO$_3$ and 10% aqueous citric acid, dried over Na$_2$SO$_4$ and concentrated. Ether was added and the precipitated was collected by filtration. Yield 6.2 g (98.3%), mp 171°–173° C., $[\alpha]_D^{26} -15.5°$ (c=0.9, DMF), $Rf^1$ 0.64.

Elemental analysis: Calcd. for $C_{46}H_{65}O_9N_7S$: C, 61.93; H, 7.34; N, 10.99; S, 3.59; Found: C, 62.02; H, 7.37; N, 11.08; S, 3.59

(viii) Production of Boc-Met-Leu-Phe-Arg(Pme)-Gly-OBu$^t$

Z-Leu-Phe-Arg(Pme)-Gly-OBu$^t$ (6.0 g) was catalytically reduced in 200 ml of MeOH and then dissolved in 150 ml of DMF. Boc-Met-OH (prepared from 3.0 g of Boc-Met-OH.DCHA) and 1.39 g of HONB were added and the mixture was cooled with ice. DCC (1.59 g) was added and the whole mixture was stirred for 15 hours. The formed DCU was filtered off and the filtrate was concentrated. The residue was dissolved in n-BuOH-AcOEt and the solution was washed with 10% aqueous citric acid, dried over Na$_2$SO$_4$ and concentrated. Ether was added and the crystals was collected by filtration. Yield 6.2 g (93.1%), mp 192°–195° C., $[\alpha]_D^{26} -19.7°$ (c=1.0, DMF), $Rf^1$ 0.64.

Elemental analysis: Calcd. for $C_{48}H_{76}O_{10}N_8S_2$: C, 58.27; H, 7.74; N, 11.33; S, 6.48; Found: C, 58.48; H, 7.79; N, 11.34; S, 5.98

(ix) Production of Boc-Gln-Met-Leu-Phe-Arg(Pme)-Gly-OH

To 5.5 g of Boc-Met-Leu-Phe-Arg(Pme)-Gly-OBu$^t$ was added 50 ml of TFA and the mixture was shaken at room temperature for 10 minutes and then concentrated. Ether was added and the precipitate was collected by filtration and dried. It was dissolved in 50 ml of DMF and the solution was cooled with ice, followed by addition of 1.8 ml of TEA. Boc-Gln-ONB (prepared from 1.85 g of Boc-Gln-OH, 1.49 g of HONB and 1.90 of DCC) was added and the mixture was stirred for 15 hours and concentrated. AcOH and then AcOEt were added and the resulting precipitate was collected by filtration. Yield 5.3 g (89.8%), mp 181°–183° C. (decomp.), $[\alpha]_D^{26} -9.6°$ (c=1.0, DMF), $Rf^1$ 0.30.

Elemental analysis: Calcd. for $C_{49}H_{76}O_{12}N_{10}S_2$: C, 55.45; H, 7.22; N, 13.20; S, 6.04; Found: C, 55.39; H, 7.17; N, 13.34; S, 6.20

(x) Production of Z-Ser-NHNH-Boc

Z-Ser-OH (10.0 g) and 6.2 g of t-butyl carbazate were dissolved in 150 ml of DMF and the solution was ice-cooled. HONB (8.0 g) and 9.3 g of DCC were added and the mixture was stirred for 15 hours. The formed DCU was filtered off and the filtrate was concentrated. The residue was extracted into AcOEt and the AcOEt solution was washed with 4% aqueous NaHCO$_3$ and 10% aqueous citric acid, dried over Na$_2$SO$_4$ and concentrated. Ether was added and the crystals was collected by filtration. Yield 7.3 g (50.4%), mp 95°–98° C., $[\alpha]_D^{26} -6.2°$ (c=0.8, DMF), Rf$^1$ 0.62.

Elemental analysis: Calcd. for C$_{16}$H$_{23}$O$_6$N$_3$: C, 54.38; H, 6.56; N, 11.89; Found: C, 54.77; H, 6.88; N, 12.29.

(xi) Production of Z-Arg(Pme)-Ser-NHNH-Boc

Z-Ser-NHNH-Boc (3.9 g) was catalytically reduced in 300 ml of MeOH and then dissolved in 50 ml of DMF. Z-Arg(Pme)-OH [prepared from 6.2 g of Z-Arg(Pme)-OH.CHA] and 1.5 g of HOBt were added and the mixture was ice-cooled. DCC (2.3 g) was added and the whole mixture was stirred for 15 hours. The formed DCU was filtered off and the filtrate was concentrated. The residue was dissolved in AcOEt and the AcOEt solution was washed with 4% aqueous NaHCO$_3$ and 10% aqueous citric acid, dried over Na$_2$SO$_4$ and concentrated. Ether was added and the resulting precipitate was collected by filtration. Yield 7.45 g (93.7%), mp 100°–101° C., $[\alpha]_D^{26} -0.9°$ (c=1.2, DMF), Rf$^1$ 0.51.

Elemental analysis: Calcd. for C$_{33}$H$_{49}$O$_9$N$_7$S: C, 55.06; H, 6.86; N, 13.62; S, 4.46; Found: C, 55.49; H, 6.94; N, 13.14; S, 3.86

(xii) Production of Z-Lys(Mtr)-Arg(Pme)-Ser-NHNH-Boc

Z-Arg(Pme)-Ser-NHNH-Boc (3.9 g) was dissolved in 300 ml of MeOH and catalytic reduction was carried out. The product was dissolved in 50 ml of DMF, and Z-Lys(Mtr)-OH [prepared from 3.4 g of Z-Lys(Mtr)-OH.DCHA] and 0.88 g of HOBt were added. The mixture was ice-cooled and 1.34 g of DCC was added. The whole mixture was stirred for 20 hours. The formed DCU was filtered off and the filtrate was concentrated. AcOEt was added and the powdery precipitate was collected by filtration and recrystallized from MeOH-AcOEt. Yield 5.1 g (93.4%), mp 103°–105° C., $[\alpha]_D^{26} -7.2°$ (c=0.8, DMF), Rf$^1$ 0.57.

Elemental analysis: Calcd. for C$_{49}$H$_{73}$O$_{13}$N$_9$S$_2$: C, 55.50; H, 6.94; N, 11.89; S, 6.05; Found: C, 55.70; H, 7.15; N, 11.60; S, 5.63

(xiii) Production of Z-Arg(Pme)-Lys(Mtr)-Arg(Pme)-Ser-NHNH-Boc

Z-Lys(Mtr)-Arg(Pme)-Ser-NHNH-Boc (4.8 g) was dissolved in 300 ml of MeOH and catalytic reduction was carried out. The product was dissolved in 70 ml of DMF, and Z-Arg(Pme)-OH [prepared from 2.8 g of Z-Arg(Pme)-OH.CHA] and 0.74 g of HOBt were added. The mixture was ice-cooled and 1.12 g of DCC was added. The whole mixture was stirred for 15 hours. The formed DCU was filtered off and the filtrate was concentrated. The residue was dissolved in AcOEt and the AcOEt solution was washed with 4% aqueous NaHCO$_3$ and 10% aqueous citric acid, dried over Na$_2$SO$_4$ and concentrated. Ether was added and the resulting precipitate was collected by filtration and re-precipitated from MeOH-ether. Yield 5.8 g (89.8%), mp 136°–137° C., $[\alpha]_D^{26} -6.6°$ (c−1.0, DMF), Rf$^1$ 0.58.

Elemental analysis: Calcd. for C$_{66}$H$_{99}$O$_{16}$N$_{13}$S$_3$: C, 55.56; H, 6.99; N, 12.76; S, 6.74; Found: C, 55.34; H, 7.07; N, 12.50; S, 6.59

(xiv) Production of Z-Lys(Mtr)-Arg(Pme)-Lys(Mtr)-Arg(Pme)-Ser-NHNH-Boc

Z-Arg(Pme)-Lys(Mtr)-Arg(Pme)-Ser-NHNH-Boc (3.0 g) was dissolved in 150 ml of MeOH and catalytic reduction was carried out. The product was dissolved in 60 ml of DMF, and Z-Lys(Mtr)-OH [prepared from 1.54 g of Z-Lys(Mtr)-OH.DCHA] and 0.31 g of HOBt were added. The mixture was ice-cooled and 0.57 g of DCC was added. The whole mixture was stirred for 15 hours. The formed DCU was filtered off and the filtrate was concentrated. The residue was dissolved in AcOEt and the AcOEt solution was washed with 4% aqueous NaHCO$_3$ and 10% aqueous citric acid, dried over Na$_2$SO$_4$ and concentrated. Ether was added and the crystalline precipitate was collected by filtration and recrystallized from AcOEt. Yield 2.70 g (72.8%), mp 123°–125° C., $[\alpha]_D^{26} -5.9°$ (c=1.1, DMF), Rf$^1$ 0.57.

Elemental analysis: Calcd. for C$_{82}$H$_{123}$O$_{20}$N$_{15}$S$_4$: C, 55.73; H, 7.02; N, 11.89; S, 7.26; Found: C. 55.89; H, 7.30; N, 11.72; S, 7.08

(xv) Production of Boc-Gln-Met-Leu-Phe-Arg(Pme)-Gly-Arg(Pme)-Arg(Pme)-Ala-Ser-Gln-OBu$^t$ Z-Arg(Pme)-Arg(Pme)-Ala-Ser-Gln-Obu$^t$ (1.0 g) was dissolved in 100 ml of MeOH and catalytic reduction was carried out. The product was then dissolved in 20 ml of DMF, and 0.85 g of Boc-Gln-Met-Leu-Phe-Arg(Pme)-Gly-OH obtained in Reference Example 1 (ix) and 135 mg of HOBt were added. The mixture was ice-cooled and 210 mg of DCC was added. The whole mixture was stirred for 20 hours. The formed DCU was filtered off and the filtrate was concentrated. MeOH was added and the resulting precipitate was collected by filtration. Yield 1.50 g (87.4%), mp 216°–217° C. (decomp.), $[\alpha]_D^{26} -11.8°$ (c=1.0, DMF), Rf$^1$ 0.43.

Elemental analysis: Calcd. for C$_{98}$H$_{154}$O$_{23}$N$_{22}$S$_4$: C, 55.09; H, 7.27; N, 14.42; S, 6.00; Found: C, 54.81; H, 7.33; N, 14.23; S, 5.79

(xvi) Production of H-Lys-Arg-Lys-Arg-Ser-Gln-Met-Leu-Phe-Arg-Gly-Arg-Arg-Ala-Ser-Gln-OH To 1.0 g of Boc-Gln-Met-Leu-Phe-Arg(Pme)-Gly-Arg(Pme)-Arg(Pme)-Ala-Ser-Gln-OBu$^t$ was added 10 ml of TFA and the mixture was shaken at room temperature for 50 minutes and then concentrated. Ether was added and the precipitate was collected by filtration and dried.

Separately, 10 ml of TFA was added to 0.83 g of Z-Lys(Mtr)-Arg(Pme)-Lys(Mtr)-Arg(Pme)-Ser-NHNH-Boc and the mixture was shaken at room temperature for 10 minutes and then concentrated. Ether was added and the precipitate was collected by filtration and dried. It was dissolved in 10 ml of DMF and the solution was cooled with dry ice-acetone, followed by addition of 0.23 ml of 6.2N HCl/AcOEt and isoamyl nitrite (0.075 ml). The temperature was maintained at −25° to −20° C. for 20 minutes (negative to the hydrazine test) and the reaction mixture was cooled again with dry ice-acetone and then neutralized with 0.25 ml of TEA. The amine component was dissolved in 40 ml of DMF and the solution was ice-cooled. TEA (0.16 ml) was added and the above azide solution was added. The whole mixture was stirred at 4° C. for 72 hours and poured into diluted acetic acid. The formed precipitate was collected by filtration and washed with aqueous CH$_3$CN. Yield 1.40 g (81.5%),Rf$^1$ 0.09. A part (400 mg) of this product was dissolved in 60 ml of TFA-thioanisole-methyl sulfide (8:1:1) containing 0.15M MSA and the solution was shaken at room temperature for 2 hours. AcONH$_4$ (400 mg) was added and the mixture was concentrated. Ether was added and the precipitate was collected by filtration and dried. It was dissolved in a small amount of 1N AcOH and the solution was passed through a Sephadex G-25 column (2.2×120 cm) using 1N AcOH as the eluent. Fractions from 160 ml to 260 ml were combined and lyophilized. The lyophilizate was then passed through a column of Amberlite IRA-410 (acetate form) and lyophilized. This lyophilizate was purified by HPLC using a TSK-LS-410 column (2.14×7.5 cm+2.14×30 cm) to give the above-identified compound. Yield 45 mg, $[\alpha]_D^{24}$ −45.9° (c=0.7, 0.1N AcOH), Rf$^4$ (cellulose) 0.20.

Amino acid analysis: Lys 1.71, Arg 4.71, Ser 1.69, Glu 2.12, Gly 1.00, Ala 1.03, Met 0.32, Leu 1.30, Phe 1.08 (average recovery rate 77%).

EXAMPLE 2

Synthesis of carrier protein-polypeptide complex for raising antibody

The polypeptide obtained in Example 1 (xvi) was coupled with thyroglobulin (hereinafter, TG) according to Goodfriend et al. [Science, 144, 1334 (1964)]. Thus, 2.5 mg of said polypeptide was mixed with 3.75 mg of TG and, following addition of 2 ml of 50 mM phosphate buffer, the mixture was stirred well in ice water. Thereto was gradually added drop by drop a solution of 30.4 mg of carbodiimide hydrochloride in 200 ml of distilled water. Thereafter, the mixture was stirred in ice-water for 3 hours. After the reaction, dialysis was performed against distilled water to a sufficient extent, followed by lyophilization to give 4.7 mg of a protein complex.

EXAMPLE 3

Preparation of enzyme-linked antigen for antibody detection by EIA

The enzyme-linked antigen for EIA was prepared according to Kitagawa et al. [Journal of Biochemistry, 79, 233, (1976)].

(i) Introduction of a maleimido group into the polypeptide

The polypeptide (350 nmoles) as obtained in Example 1 (xvi) was dissolved in 1 ml of 100 mM phosphate buffer (pH 6.8, and the solution was added to a solution of 585 μg (1.75 μmoles) of N-(4-carboxycyclohexylmethyl)maleimide N-hydroxysucciinimide ester in 70 μl of N,N-dimethylformamide. The mixture was stirred at 30° C. for 30 minutes. After the reaction, fractionation was performed using a Sephadex G-25 column to give 185 nmoles of a polypeptide fraction with the maleimido group introduced therein.

(ii) Coupling of the maleimido-group-containing polypeptide with β-D-galactosidase The maleimido-containing polypeptide (16.5 nmoles) as obtained in Example 3(i) was mixed with 3.3 nmoles of β-D-galactosidase. After 18 hours of reaction at 4° C., 412.5 nmoles of β-mercaptoethanol was added for teminating the reaction. The β-D-galactosidase-coupled polypeptide was fractionated on a Sepharose 6B column and used for the subsequent experiments.

EXAMPLE 4

EIA method fpr detecting antibody

The detection of antibody activity in the serum of mice immunized with the protein complex obtained in Example 2 or in the hybridoma supernatant was conducted by the EIA method [Immunopharmacology, 1, 3, (1978)]. Thus, the serum or hybridoma supernatant was diluted with buffer A (20 mM Na$_2$HPO$_4$, 100 mM NaCl, 0.1% NaN$_3$, 1 mM MgCl$_2$, pH 7.0), a 100-μl portion of the dilution was mixed with 100 μl of the polypeptide derivative as obtained in Example 3, and the reaction was allowed to proceed at 24° C. for 24 hours. Thereafter, 100 μl of 3% cellulose coupled with rabbit anti-mouse IgG was added, and the reaction was allowed to proceed at 24° C. for 4 hours. After the reaction, the cellulose was washed well with buffer A containing 0.5% of Tween 20, then 500 μl of 20 μg/ml 4-methylumbelliferyl-β-D-galactoside was added and, after 2 hours of reaction at 37° C., 3 ml of 100 mM carbonate buffer (pH 10.5) was added for terminating the reaction. The fluorescence intensity was measured with a fluorometer (excitation: 365 nm; emission: 450 nm).

EXAMPLE 5

Immunization

Each of 6 female BALB/C mice aged 7 to 8 weeks was subcutaneously inoculated with 40 μg (on the protein basis) of the protein complex obtained in Example 2 (as the antigen) in intimate admixture with Freund's complete adjuvant (primary immunization). Two weeks after the primary immunization, the mice were subcutaneously inoculated with the antigen at the same dose as above in intimate admixture with Freund's incomplete adjuvant (secondary immunization). Further two weeks later, a third immunization was made in the same manner as in the secondary immunization. Six days after the third immunization, partial blood sampling was made from the mice and the serum antibody titers were determined by the EIA method described in Example 4. The mouse numbered γ-2 gave the highest antibody titer and subjected to the final immunization by intravenous inoculation with 120 μg of the antigen dissolved in 0.5 ml of aqueous sodium chloride. The antibody titer data for each mouse are shown in Table 1.

TABLE 1

| | Antipeptide antibody titers in immunized mice | | |
|---|---|---|---|
| | B/T (%) | | |
| Mouse No. | Primary immunization[1] | Secondary immunization[2] | Third immunization[3] |
| γ-1 | —[4] | N.D | 24.5 |
| 2 | N.D[5] | 19.3 | 35.3 |
| 3 | — | N.D | 24.7 |
| 4 | N.D | 1.3 | 1.7 |
| 5 | N.D | 1.8 | 5.0 |
| 6 | — | N.D | 0.8 |
| Normal mouse | 0.6 | 0.1 | N.D |

[1]Serum dilution ratio: 1/1000
[2]Serum dilution ratio: 1/6300
[3]Serum dilution ratio: 1/7800
[4]—: Not detectable
[5]ND: Not determined
B/T: (Bound enzyme activity/total added enzyme activity) × 100

EXAMPLE 6

Cell fusion

Immunization was performed by the method described in Example 5. Three days after the final immunization, the spleen was excised from the γ-2 mouse, filtered under pressure through a stainless mesh, and suspended in Eagle's minimum essential medium (MEM) to give a spleen cell suspension. For cell fusion, BALB/C mouse-derived P3-x63.Ag8.U1 (P3U1) myeloma cells were used [Current Topics in Microbiology and Immunology, 81, 1, (1978)]. Cell fusion was performed by the original method [Nature, 256, 495, (1975)]. Thus, spleen cells and P3U1 cells were separately washed three times with serum-free MEM and mixed at a ratio of 5:1 (in number of cells). The mixture was centrifuged at 800 rpm for 15 minutes, whereby the cells were settled. After thorough removal of the supernatant, the sediment was lightly loosened, 0.3 ml of 45% polyethylene glycol (PEG) 6000 (Koch-Light) was added, and the mixture was allowed to stand in a warm water tank maintained at 37° C. for 7 minutes so as to effect cell fusion. Thereafter, MEM was added thereto at a rate of 2 ml per minute. After addition of 12 ml in total of MEM, the resulting mixture was centrifuged at 600 rpm for 15 minutes, followed by removal of the supernatant. The cell sediment was suspended in RPMI-1640 medium supplemented with 10% fetal calf serum (RPMI1640-10FCS) in a concentration of $2 \times 10^5$ P3U1 cells/ml and each of 144 wells on 24-well multidishes (Linbro) was seeded with 1 ml of the suspension. After seeding, the cells were incubated at 37° C. in a 5% carbon dioxide gas incubator. After 24 hours, HAT-selective culture was started by adding RPMI1640-10FCS medium supplemented with HAT ($1 \times 10^{-4}$M hypoxanthine, $4 \times 10^{-7}$M aminopterin, $1.6 \times 10^{-5}$M thymidine) (HAT medium) in an amount of 1 ml per well. The HAT-selective culture was continued while 1 ml of the old medium was replaced by 1 ml of fresh HAT medium 3, 5 and 7 days after start of the culture. The growth of hybridomas was noted 10 to 14 days after cell fusion. When the culture broth turned yellow (about $1 \times 10^6$ cells/ml), the supernatant was collected and examined for the presence of antibody by the EIA method. In this manner, supernatants from 141 wells in which hybridoma growth had been noted were examined. Two wells (γ2-11 and γ2-100) afforded intense antibody activity and other two wells (γ2-62 and γ2-70) presented weak antibody activity.

EXAMPLE 7

Cloning

Hybridomas from 3 wells (γ2-11, 62 and 100) which were positive in antibody activity were cloned by the limiting dilution method. Thus, hybridomas were suspended in RPMI1640-20FCS in a concentration of 2 hybridomas/ml and the suspension was distributed in 0.1-ml portions into the wells on 96-well microplates (Nunc). In said distribution, $5 \times 10^5$ per well of BALB/c mouse thymocytes were added as feeder cells. As a result, cell proliferation was observed in about 2 weeks. The supernatant was then collected and examined for the presence of antibodies by the EIA method as described in Example 4. Antibody activity was noted in 8 out of 19 clones from γ2-11 in 3 out of 54 clones from γ262 and in 5 out of 47 clones from γ2-100 (Table 2).

TABLE 2

| Anti-peptide antibody activity of cloned hybridomas | |
|---|---|
| Hybridoma No. | B/T (%) |
| γ2-11 | |
| 1 | 68 |
| 2 | 31 |
| 3 | 63 |
| 6 | 68 |
| 7 | 67 |
| 9 | 69 |
| 12 | 42 |
| 18 | 60 |
| γ2-62 | |
| 14 | 20 |
| 16 | 21 |
| 34 | 16 |
| γ2-100 | |
| 2 | 69 |
| 3 | 70 |
| 16 | 56 |
| 25 | 80 |
| 46 | 33 |
| Hyperimmune mouse serum | 35 |

B/T: (Bound enzyme activity/total added enzyme activity) × 100

EXAMPLE 8

Binding capacity of monoclonal antibody to IFN-γ

The binding capacity of monoclonal antibody to IFN-γ was determined by the following method. To 300 μl of a 3% solution of cellulose coupled with rabbit anti-mouse IgG antibody, 300 μl of the culture supernatant of each of 2 or 3 cloned cell lines from each of γ2-11, γ2-62 and γ2-100 was added, and the reaction was allowed to proceed at room temperature for 12 to 20 hours. Thereafter, the cellulose was thoroughly washed with physiological saline, and 550 U/ml of IFN-γ obtained by the procedure mentioned below was added thereto. After 3 to 4 hours of reaction, the supernatant was collected and the IFN-γ activity therein was determined by the cytopathic effect (CPE) reading method using a microplate [Applied Microbiology, 16, 1706, (1968)]. Thus, 50 μl of MEM was placed in each well of a 96-well microplate (Nunc) and 50 μl of the IFN sample was added to the first well, followed by serial two-fold dilution. To each well thus prepared, 50 μl of a WISH cell suspension ($4 \times 10^5$ cells/ml) in 20% FCS-containing MEM was added, and incubation was conducted in a carbon dioxide gas incubator at 37° C. for 24 hours. Thereafter, 50 μl of a vesicular stomatitis virus (New Jersey strain) preparation adjusted to a concentration of 2000TCID$_{50}$ (TCID$_{50}$: median tissue culture infecting dose) was added to each well and incubation was performed in a carbon dioxide incubator at 37° C. About 35 hours later, when cells in the IFN sample-free well showed 100% CPE, each well was microscopically observed for the estimation of CPE, and the reciprocal of the dilution factor for the IFN sample in that well in which 50% CPE was noted was referred to as the IFN titer.

The IFN-γ sample used was the supernatant collected 72 hours after stimulation of human peripheral lymphocytes with 40 μg/ml of concanavalin A and 15 ng/ml of 12-0-tetradecanoylphorbol-13-acetate. Each ml of this culture supernatant contained 4400 units of human IFN-γ (heat- and acid-labile). If antibodies having binding capacity to IFN-γ are present in the cloned cell culture supernatant, then the added IFN-γ should bind to the antibodies on cellulose and reduction in IFN-γ activity of the supernatant should occur. As a result, for the clone γ2-11, relatively intense binding activity to IFN-γ was noted and 50-75% of the added IFN-γ (550 U/ml) bound to antibodies (Table 3).

TABLE 3

| Hybridoma culture supernatant | Absorption of IFN-γ activity by monoclonal antibodies | |
|---|---|---|
| | Residual IFN activity (U/ml) | |
| | Experiment 1 | Experiment 2 |
| γ2-11.1 | 138 | 275 |
| γ2-11.2 | 207 | N.D. |
| γ2-11.6 | N.D. | 275 |
| γ2-62.2 | 275 | 550 |
| γ2-62.3 | 275 | 550 |
| γ2-100.2 | 550 | N.D. |
| γ2-100.3 | 550 | N.D. |
| — | 550 | 550 |

N.D.: not done

EXAMPLE 9

Ascites formation by monoclonal antibody-producing hybridomas

Ascites formation was caused by intraperitoneal inoculation of BALB/c mice intraperitoneally pretreated with 0.5 ml of mineral oil with $1 \times 10^6$ γ2-11.1 clone cells (Mouse B hybridoma γ2-11.1) capable of producing antibodies having IFN-γ-binding activity. Ten days after intraperitoneal administration of hybridomas, the ascitic fluid was taken and examined for antibody activity up to $10^7$-fold dilution. While the antibody activity of the corresponding clone cell culture supernatant was detected up to $10^4$-fold dilution, the formation of ascites (ascitization) led to an about 1000 times increase in antibody activity.

EXAMPLE 10

Monoclonal antibody purification

Figure 2:
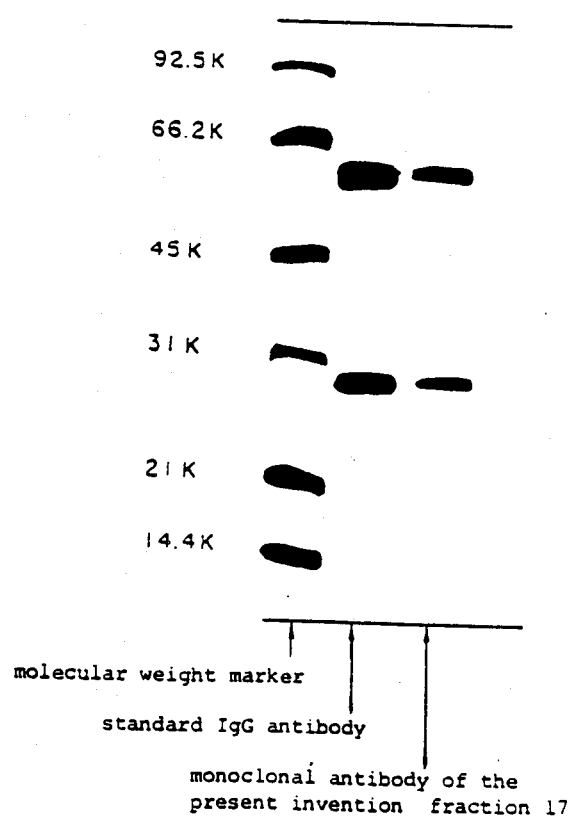
FIG. 2 shows the results of the electrophoresis of the monoclonal antibody in Example 10.

Using 4 ml of the ascitic fluid obtained in Example 9 as the starting material, monoclonal antibody purification was performed by the method of Staehelin et al. [Journal of Biological Chemistry, 256, 9750, (1981)]. Thus, the ascitic fluid was first centrifuged at 10,000 rpm for 15 minutes to remove fibrin-like substances therefrom and then diluted with phosphate buffer-saline (PBS: 8.1 mM $NaH_2PO_4$, 1.5 mM $KH_2PO_4$, 2.7 mM KCl, 137 mM NaCl; pH 7.2) to a concentration at which the ultraviolet absorption at 280 nm ($A_{280}$) for said dilution would range from 12 to 14. Thereafter, saturated aqueous ammonium sulfate was added to the diluted sample to a concentration of 47%. The mixture was stirred at 4° C. for 60 minutes to effect salting out and then centrifuged (10,000 rpm, 15 minutes) to give a precipitate. The precipitate was dissolved in 20 mM Tris buffer (pH 7.9) containing 50 mM NaCl and dialyzed against 2 liters of the same buffer. Two hours later, the dialyzing solution was replaced by a fresh 2-liter portion of the same solution and the dialysis was continued for further 15 hours. Thereafter, the precipitate was removed by centrifugation at 10,000 rpm for 15 minutes, and the supernatant was adjusted to a concentration such that the $A_{280}$ value became 20-30. This sample was subjected to fractionation on a DEAE-cellulose column (8 ml, Whatman $DE_{52}$) equilibrated with a sufficient amount of Tris buffer containing 50 mM NaCl. After extensive washing with the same buffer at a flow rate of 1.5 ml/min, NaCl concentration was linearly increased from 50 mM to 500 mM. Under these conditions, the antibody activity was detected mainly in effluent fractions (FIG. 1). Confirmation that the purified sample is antibody was made by SDS-polyacrylamide gel electrophoresis (SDS-PAGE) method as described by Laemmli et al. [Nature, 227, 680, (1970)]. Thus, some of the fractions obtained by ammonium sulfate salting out and DEAE-cellulose fractionation were each subjected to reduction with 2-mercaptoethanol, followed by 17% SDS gel electrophoresis at 30 volts for 24 hours. In agreement with the antibody activity peaks, two bands were noted at positions corresponding to molecular weights of about 55 kilodaltons (H chain) and about 28 kilodaltons (L chain) (FIG. 2). The thus-purified antibody fraction 17 was examined for IFN-γ-binding activity by adding IFN-γ (2200 U/ml) as described in Example 8. It was thus found that about 50% of IFN-γ was bound to the antibody (Table 4).

TABLE 4

| Sample | Dilution | Residual IFN activity (U/ml) |
|---|---|---|
| γ2-11.1 fraction 17 | $10^{-1}$ | 1100 |
| | $10^{-2}$ | 1100 |
| | $10^{-3}$ | 2200 |
| | $10^{-4}$ | 2200 |
| Anti-IgE monoclonal antibody (control) | $10^{-1}$ | 2200 |
| | $10^{-2}$ | 2200 |
| | $10^{-3}$ | 2200 |
| | $10^{-4}$ | 2200 |

EXAMPLE 11

Subclass to which monoclonal antibodies belong

The fraction 17 purified by the method of Example 10 was diluted 10 times and subjected to immuno-precipitation reaction in agar (Ouchterlony test: Immunological Methods, Gel-Diffusion Technique, Blackwell, Oxford, 1964) using goat anti-mouse IgG1, G2a, and G3 antibodies (Miles) so the IgG subclass to which γ2-11.1 monoclonal antibody might belong could be identified. A single distinct band was found between the monoclonal antibody and the goat anti-mouse IgG2b antibody, while no band formation was noted between the monoclonal antibody and other anti-IgG antibodies. Accordingly, said monoclonal antibody was found to belong to IgG2b (Table 5).

TABLE 5

| Monoclonal antibody subclass | | |
|---|---|---|
| Antigen | Antibody | Precipitation curve |
| Monoclonal antibody of the present invention (fraction 17) | Anti-IgG1 | — |
| Monoclonal antibody of the present invention (fraction 17) | Anti-IgG2a | — |
| Monoclonal antibody of the present invention (fraction 17) | Anti-IgG2b | + |
| Monoclonal antibody of the present invention (fraction 17) | Anti-IgG3 | — |

EXAMPLE 12

Preparation of antibody column

Twenty-five ml (65.3 mg) of the monoclonal antibody from the effluent fractions as purified by the procedure of Example 10 was dialyzed overnight against 0.1M $NaHCO_3$ (pH 8.3). Separately, 25 ml of AFFI-GEL 10 (Bio-Rad) was thoroughly washed with water using a glass filter, suspended in 0.1M $NaHCO_3$ (pH 8.3) and mixed with the above antibody. The mixture was stirred gently at 4° C. for 4 hours to effect the reaction, and then allowed to stand at 4° C. overnight. The resulting AFFI-GEL 10 was washed well with 0.1M NaHCO₃ (pH 8.3) using a glass filter. To the gel was added 25 ml of a solution (pH 8.0) containing 0.1M ethanolamine and 0.15M NaCl. The mixture was shaken at 4° C. for an hour so as to block possibly remaining unreacted active groups. Then, the gel was washed well with PBS, and suspended in 25 ml of 0.1% NaN₃-containing PBS. The suspension was stored at 4° C. Based on the amount of the added antibody and the amount of the antibody in the recovered filtrate, it was found that the antibody was conjugated to the gel in a proportion of 2.35 mg/ml of gel. A column was packed with the reaction product obtained in this manner and used as an antibody column.

EXAMPLE 13

Sixty ml of the supernatant obtained in Reference Example 4 was diluted with 20 mM Tris-HCl containing 1 mM EDTA and 0.15M NaCl (pH 7.6) (TEN) to make 150 ml and the dilution was submitted to an anti-IFN-γ antibody column (9 ml) prepared by the method of Example 12. The column was washed well with TEN and further with TEN containing 0.01% Nonidet P-40 (Shell) and 0.5M NaCl. Then, IFN-γ was eluted with 0.1M acetic acid containing 0.25M NaCl. The eluate was immediately neutralized with 1M Tris-HCl (pH 7.6). The resulting solution was dialyzed against distilled water at 4° C. for 16 hours and, after freezing with acetone-dry ice, lyophilized to give a powder.

The results obtained are shown below.

|  | Protein (mg) | Total activity (U) | Specific activity (U/mg) | Recovery (%) |
|---|---|---|---|---|
| Supernatant of lysate | 250.8 | $4 \times 10^8$ | $1.6 \times 10^6$ | — |
| After treatment on antibody column | 2.0 | $1.5 \times 10^8$ | $7.5 \times 10^7$ | 37.5 |

The specific activity of the final human immune interferon protein product thus obtained [based on the viral activity determination by the cytopathic effect inhibition assay using VSV and WISH cells (described previously herein)] was $7.5 \times 10^7$ U/mg. The characterization of this protein is mentioned below. Characterization of human immune interferon protein

(i) Molecular weight

Figure 3:
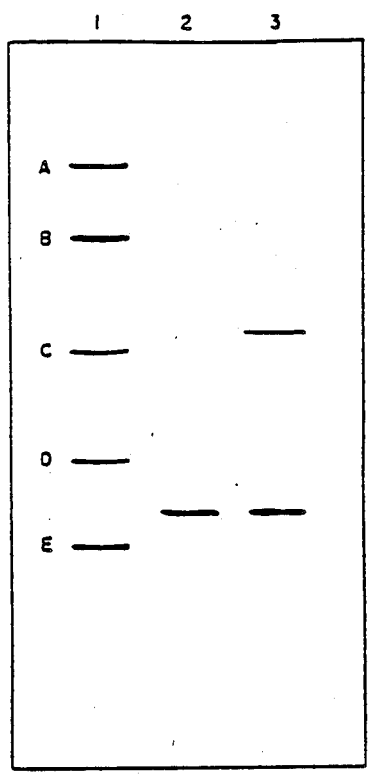
FIG. 3 shows the results of electrophoresis of the human immune interferon protein obtained by the purification method in accordance with the present invention as mentioned following Example 13.
Figure 4:
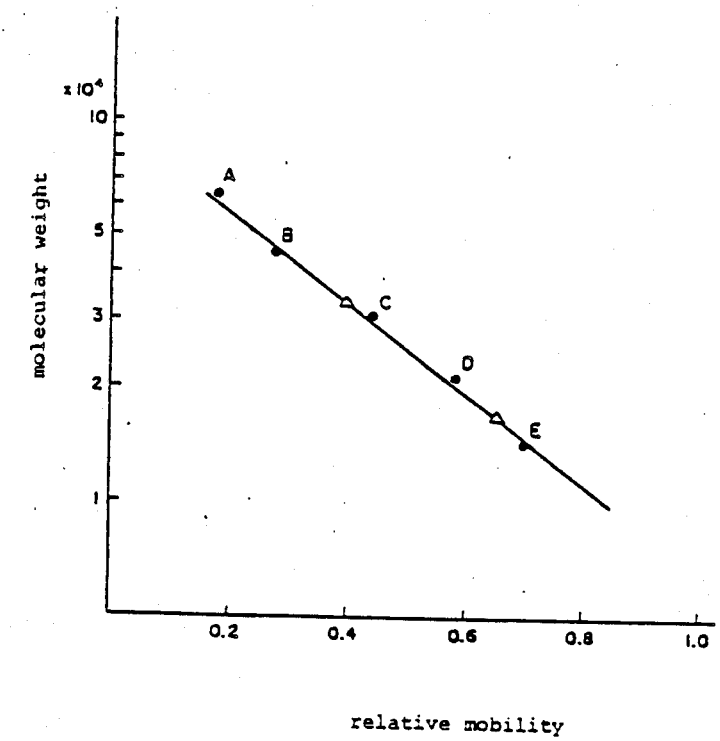
FIG. 4 shows the results of the molecular weight determination also mentioned following Example 13.

The protein obtained in Example 13 was treated with 2-mercaptoethanol, subjected to SDS-polyacrylamide gel (17.5%) electrophoresis (15 mV, 6 hours) and stained with Coomassie blue. The protein could be identified as a single band (FIG. 3). From the relation between the migratin distance for the molecular weight markers simultaneously subjected to electrophoresis and the migration distance for the protein, the molecular weight of the protein was estimated at 17,000±1,000 (FIG. 4). For the protein not treated with 2-mercaptoethanol, an additional band was detected at a position corresponding to a molecular weight of 33,000±2,000. This value is about two times the molecular weight of IFN-γ, namely 17,000±1,000, suggesting that the band is due to dimerized IFN-γ.

(ii) Amino acid analysis

An aliquot of the protein obtained in Example 13 was placed in a glass tube for hydrolysis and a 200 times (V/W) amount of constant boiling point hydrochloric acid containing 4% thioglycolic acid was added. The tube was sealed under reduced pressure and hydrolysis was conducted at 110° C. for 24, 48 and 72 hours. After each hydrolysis, the tube was opened, the hydrochloric acid was removed under reduced pressure, and the residue was dissolved in 0.02N hydrochloric acid and analyzed using a Hitachi Model 835 high-speed amino acid analyzer.

For the determination of cystine and cysteine, the above protein ws oxidized with performic acid according to Hirs et al. (Methods in Enzymology, 11, 197, (1967)] and hydrolyzed in the same manner as above for 24 hours, and cysteic acid was quantitatively determined by using the amino acid analyzer. The mean of three values obtained after 24, 48 and 72 hours of hydrolysis was employed as the found value for each amino acid except for the cases of serine, threonine, thyrosine and tryptophan, where the values were estimated by extrapolation of the hydrolysis period to 0 hour. The results are shown in Table 6.

TABLE 6

| Amino acid detected | Mole % | Amino acid detected | Mole % |
|---|---|---|---|
| Aspartic acid | 13.4 | Methionine | 2.9 |
| Threonine | 3.6 | Isoleucine | 4.8 |
| Serine | 7.4 | Leucine | 6.8 |
| Glutamic acid | 12.5 | Thyrosine | 3.4 |
| Proline | 1.4 | Phenylalanine | 6.7 |
| Glycine | 3.8 | Lysine | 13.5 |
| Alanine | 5.3 | Histidine | 1.5 |
| Cysteic acid | 1.3 | Arginine | 5.4 |
| Valine | 5.7 | Tryptophan | 0.9 |

(iii) Amino terminal amino acid analysis

The protein obtained in Example 13 was oxidized with performic acid according to Hirs et al. [Methods in Enzymology, 11, 197, (1967)] and then subjected to amino terminal amino acid analysis by the modified Edman degradation method of Iwanaga et al. [Eur. J. Biochem., 8, 189, (1969)]. The resulting phenylthiohydantoin-amino acids [PTH-amino acids) were identified and quantitatively determined on a Varian (USA) Model 5040 high performance liquid chromatograph using an Ultrasphere-ODS column (Altex, USA; 4.6×250 mm, particle size 5 μm) by the method of Archer et al. Altex Chromatogram, 3, 8, (1980)]. As a result, PTH-methionine sulfone and PTH-cysteic acid were detected.

As is evident from the above-mentioned examples, the purification method according to the present invention can produce substantially pure human immune interferon proteins having a specific activity of not less than $7.5 \times 10^7$ U/mg.

The results obtained with the monoclonal antibodies from γ-3 mice are described in the following.

EXAMPLE 14

Immunization

A fourth immunization was performed in the γ-3 mouse listed in Table 1 in the same manner as the second and third immunizations in Example 5. Two weeks after the fourth immunization, a final immunization was conducted in the same manner as in Example 5 by intravenous inoculation with 120 μg of the antigen dissolved in 0.5 ml of saline.

EXAMPLE 15

Cell fusion

Spleen was excised from the γ-3 mouse 3 days after the final immunization described in Example 14, and cell fusion and HAT selection culture were carried out by the procedure of Example 6. As a result, hybridoma growth was noted in 43 wells. Antibody assay by the EIA method described in Example 4 revealed strong antibody activity in two wells (γ3-11 and γ3-19).

EXAMPLE 16

Cloning

The hybridomas in the two wells (γ3-11 and γ3-19) which showed strongly positive antibody activity were cloned by the procedure of Example 7. Antibody activity was noted in 9 clones out of 21 clones for γ3-11 and in 15 clones out of 25 clones for γ3-11 (Table 7).

TABLE 7

Anti-peptide antibody activity of cloned hybridomas

| Hybridoma No. | B/T (%) |
|---|---|
| γ3-11 | |
| 1 | 82 |
| 3 | 77 |
| 4 | 71 |
| 6 | 78 |
| γ3-11 | |
| 7 | 76 |
| 8 | 19 |
| 11 | 78 |
| 12 | 71 |
| 16 | 81 |
| γ3-19 | |
| 2 | 85 |
| 3 | 88 |
| 5 | 83 |
| 7 | 80 |
| 8 | 77 |
| 12 | 75 |
| 13 | 73 |
| 14 | 76 |
| 16 | 80 |
| 17 | 81 |
| 18 | 90 |
| 19 | 85 |
| 20 | 91 |
| 23 | 81 |
| 24 | 82 |

EXAMPLE 17

Ability of the monoclonal antibodies to bind IFN-γ

The ability of the monoclonal antibodies to bind IFN-γ was investigated by the method described in Example 8. The IFN-γ sample used in this example was the product of expression in Escherichia coli of the human IFN-γ gene inserted in plasmid (recombinant IFN-γ; cf. Reference Example 4), and its concentration was adjusted to 1100 U/ml. Strong IFN-γ-binding ability was noted in the supernatants of the clones γ3-11.1 and γ3-19.20, with about 90% of IFN-γ added being bound to the antibody (Table 8).

TABLE 8

Ability of the monoclonal antibodies to absorb recombinant IFN-γ activity

| Hybridoma culture supernatant | Residual IFN activity (U/ml) |
|---|---|
| γ3-11.1 | 131 |
| γ3-19.20 | 137 |

TABLE 8-continued

Ability of the monoclonal antibodies to absorb recombinant IFN-γ activity

| Hybridoma culture supernatant | Residual IFN activity (U/ml) |
|---|---|
| — | 1100 |

EXAMPLE 18

Subclass to which monoclonal antibodies belong

The γ3-11.1 (Mouse B hybridoma γ3-11.1) and γ3-19.20 cloned cells wer ascitized by the procedure described in Example 9, and the ascites fluids obtained were purified by the procedure of Example 10. The monoclonal antibodies obtained were subclassified by the agar gel precipitin test described in Example 11. Both the monoclonal antibodies from γ3-11.1 and γ3-19.20 gave evident bands with sheep anti-mouse IgG1 antibody but no bands with other anti-IgG antibodies. It was thus revealed that the γ3-11.1 and γ3-19.20 monoclonal antibodies belong to IgG1 (Table 9).

TABLE 9

| | Monoclonal antibody subclass | |
|---|---|---|
| Antigen | Antibody | Precipitation Curve |
| γ3-11.1 | anti-IgG1 | + |
| " | anti-IgG2a | — |
| " | anti-IgG2b | — |
| " | anti-IgG3 | — |
| γ3-19.20 | anti-IgG1 | + |
| " | anti-IgG2a | — |
| " | anti-IgG2b | — |
| " | anti-IgG3 | — |

EXAMPLE 19

EIA method I for assaying IFN-γ

Assay method based on the competition for the monoclonal antibody between (a) IFN-γ sample in solution and (b) IFN-γ immobilized on a solid phase The IFN-γ expressed in Escherichia coli and purified as shown in Example 13 was suspended in phosphate buffer (pH 8.0) containing 0.1M sodium bicarbonate to make a concentration of 15 μg/ml, and 100 μl-portions of the suspension were distributed into the wells of a 96-well microplate. After 24 hours of reaction at 4° C., 100 μl-portions of 2% bovine serum albumin-containing phosphate buffer were added to the wells so as to block the remaining binding sites of the wells. After 24 hours of treatment at 4° C., the plate was subjected to ELISA. Thus, an antibody (γ3-11.1) solution (100 μl) containing the antibody in an amount of about 50% of the maximum binding amount was reacted with the recombinant IFN-γ adjusted to various concentrations (75, $3 \times 10^2$, $1.25 \times 10^3$, $5 \times 10^3$, $2 \times 10^4$, $8 \times 10^4$ U/ml) at 37° C. for an hour. The reaction mixtures were added to the above plate, and the reaction was allowed to proceed at room temperature for 3 hours. The wells were then washed with phosphate buffer, horseradish peroxidase-labelled sheep anti-mouse IgG antibody (100 μl) was added, and the reaction was allowed to proceed at room temperature for 3 hours. Thereafter, the wells were washed well with phosphate buffer, then a substrate solution (100 μl) prepared by adding 22 mg of ortho-phenylene-diamine and 10 μl of hydrogen peroxide to 10 ml of 0.1M citrate buffer was added, and the enzymatic reaction was allowed to proceed at room tempertature for 15 minutes.

Figure 9:
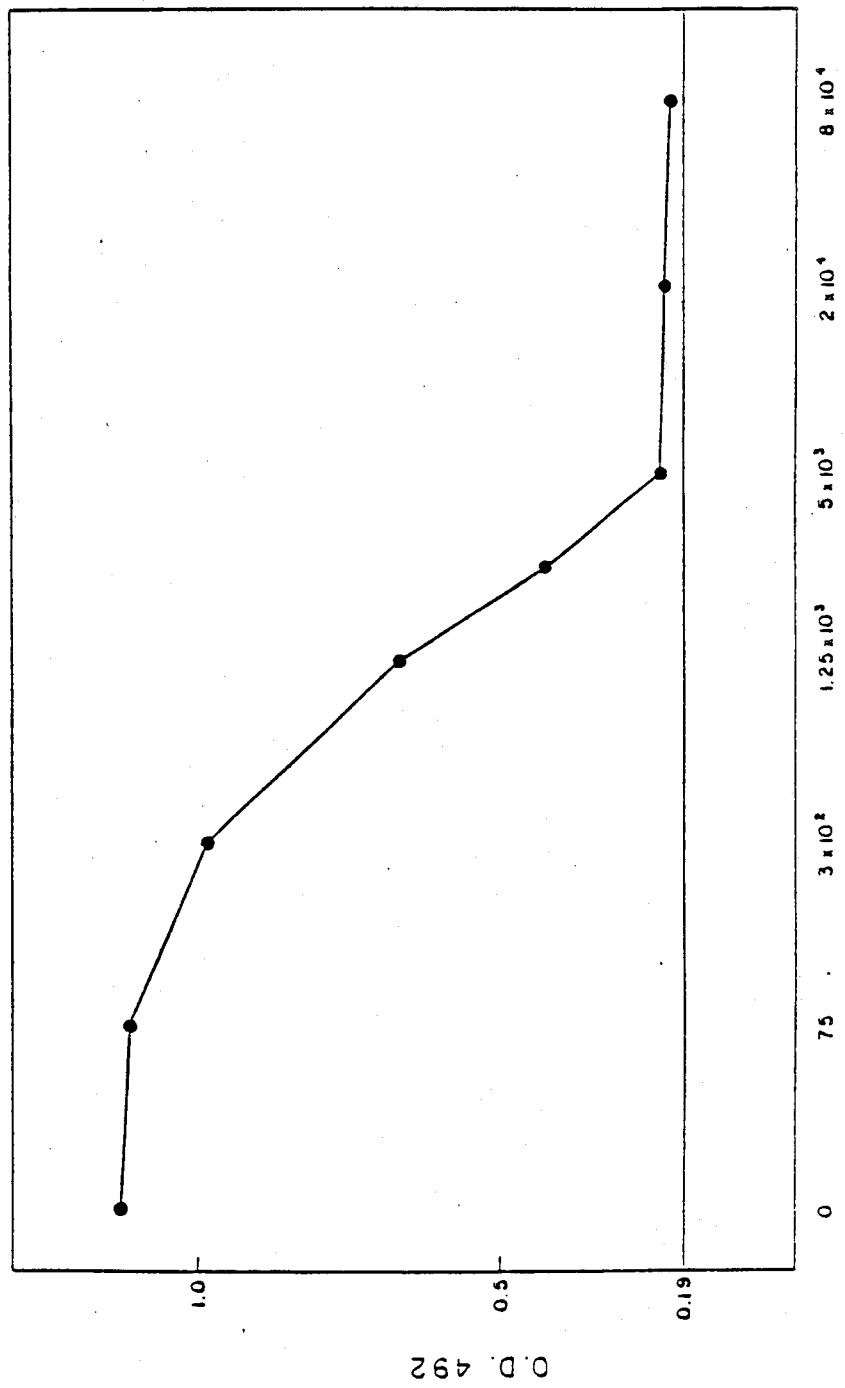
FIG. 9 shows the competition of (a) recombinant IFN-γ in solution and (b) IFN-γ immobilized on a solid phase in Example 19 for the binding of these antigens to monoclonal antibody.

Then, 4N sulfuric acid was added to terminate the reaction, and the resulting pigment was assayed at the wavelength of 492 nm using a Titertek Multiskan photometer. The results are shown in FIG. 9. It was revealed that the ELISA method can be used for the assay of IFN-γ the concentration range of $3\times10^2$ to $5\times10^3$ U/ml.

EXAMPLE 20

EIA method II for assaying IFN-γ

Assay method based on the competition for the monoclonal antibody between (a) IFN-γ sample and (b) enzyme-labelled peptide of this invention

Example 20-(i)

Figure 10:
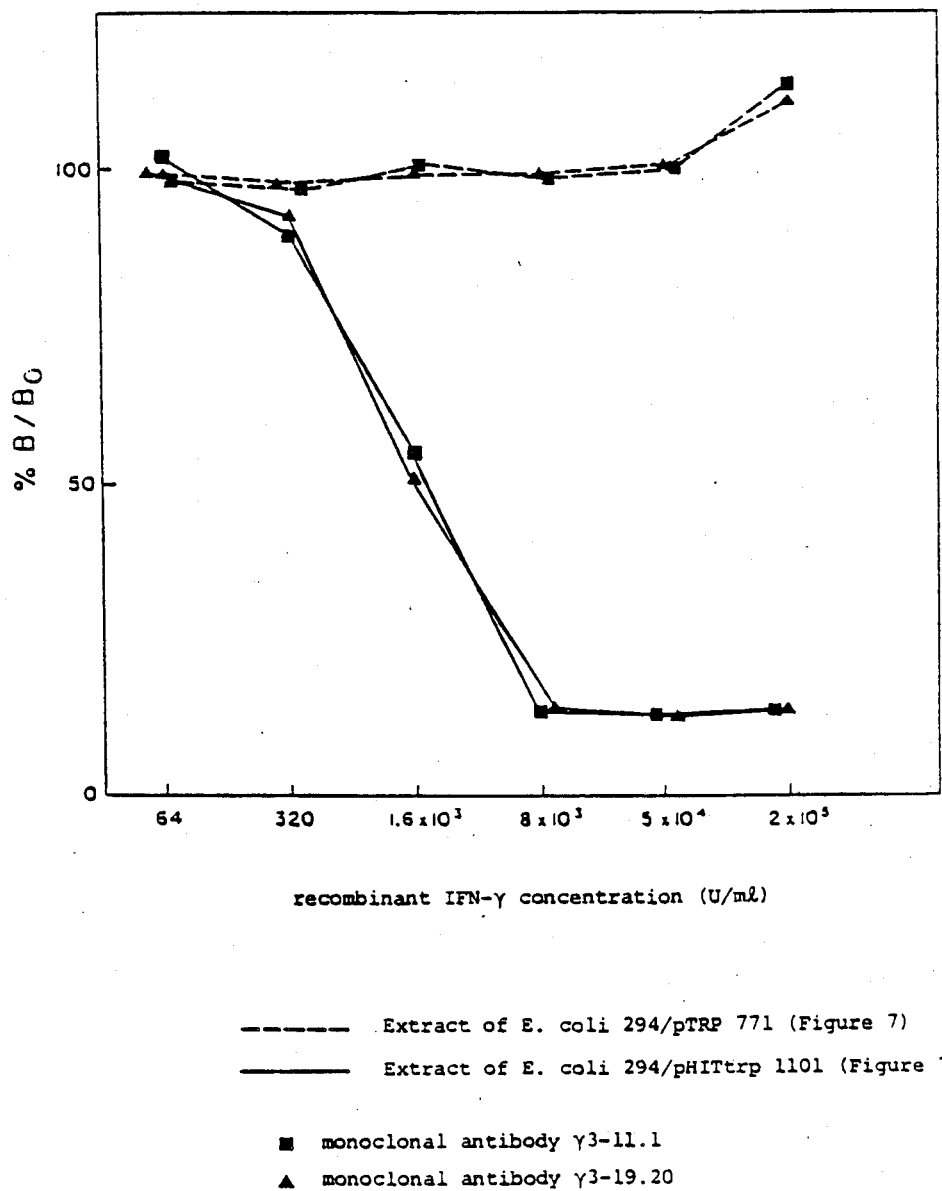
FIG. 10 and FIG. 11 show the competition of (a) IFN-γ sample and (b) enzyme-labelled peptide of this invention in Examples 20-(i) and 20(ii) for the binding of these antigens to monoclonal antibodies.

The recombinant IFN-γ obtained in Reference Example 4 was made into preparations having various concentrations (64, 320, $1.6\times10^3$, $8\times10^3$, $5\times10^4$, $2\times10^5$ U/ml), and 100 μl of each preparation was reacted with 100 μl of a solution containing a known amount of γ3-11.1 or γ3-19.20 antibody at room temperature for 2 hours. Then 100 μl of the enzyme-bound peptide derivative obtained in Example 3 was added, and the reaction was allowed to proceed at 4° C. for 48 hours. Each reaction mixture was added to 100 μl of rabbit anti-mouse IgG antibody-found 3% cellulose solution, and the reaction was allowed to proceed at room temperature for 4 hours. Thereafter, the enzymatic reaction was performed in the same manner as described in Example 4 and the fluorescence intensity was measured. The binding of the enzyme-bound polypeptide derivative to the monoclonal antibody (γ3-11.1, γ3-19.20) was slightly inhibited in the presence of 320 U/ml of IFN-γ and almost completely inhibited in the presence of $8\times10^3$ U/ml (FIG. 10). Therefore, this method can assay IFN-γ in the concentration range of 320 to $8\times10^3$ U/ml.

Example 20-(ii)

The following modification, which is based on the same principle as that in Example 20-(i) but can assay a large number of samples automatically and quickly by using Multiskan, was performed.

(1) Preparation of mouse IgG-adsorbed plate

A mouse of IgG solution (10 μg/ml, 0.01M borate buffer, pH 8.0) was distributed in 200-μl portions into the wells of a 96-well microtesting plate (Nunc-Immunoplate I, Nunc, Denmark). After allowing to stand at 4° C. overnight, the solution was removed, 300 μl of 0.02M phosphate buffer (pH 7.4) containing 1% of BSA was poured into each well and, after allowing to stand at room temperature for 3 hours, the buffer was removed.

(2) Preparation of monoclonal antibody γ3-11.1-adsorbed plate

Into each well of the mouse IgG-adsorbed plate prepared in (1), there was poured 150 μl of a 350,000-fold γ3-11.1 dilution prepared with 0.02M phosphate buffer (pH 7) containing 0.1% of BSA. After allowing to stand at 4° C. overnight, the dilution was removed, the wells were washed three times with 0.01M phosphate buffer (pH 7.4) to give an antibody-adsorbed plate.

(3) Procedure

An assay sample and a standard IFN-γ were each diluted to an adequate concentration with buffer A (0.02M pH 7 phosphate buffer containing 0.1M NaCl, 1 mM $MgCl_2$, 0.1% BSA and 0.1% $NaN_3$). The dilutions (each 75 μl) were poured into each well of the plate prepared in (2). Then, 5 μl of a 130-fold dilution of the enzyme-labelled product of Example 3 (diluent: buffer A) was poured into each well on the plate. The wells were covered with parafilm, and the reaction was allowed to proceed at 37° C. for an hour and then at room temperature for 3 hours. The reactant solution was removed, and the well were washed with four 75-μl portions of 0.01M phosphate buffer (pH 7.4).

Figure 11:
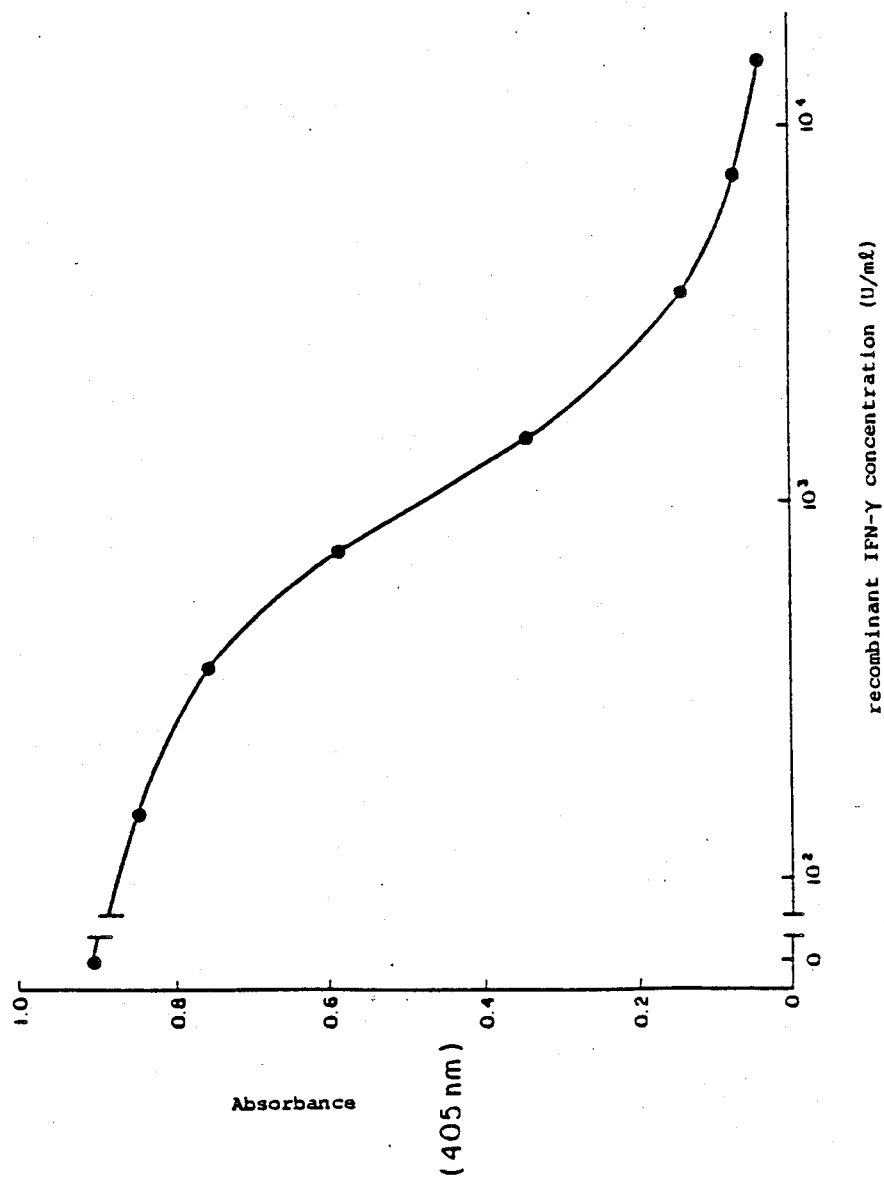

For coloration, 150 μl of a 1.5 mg/ml solution of 4-nitrophenyl-β-D-galactopyranoside (Wako Pure Chemical Industries, special grade) in buffer A was poured ito each well on the plate, and the reaction was allowed to proceed at room temperature overnight. The coloration reaction was terminated by adding 100 μl of 0.4M carbonate buffer (pH 10.5) to each well, and the absorbance at 405 nm was measured on a photometer for microtesting plates, Titertek Multiskan (Flow Laboratories, USA). A standard curve for IFN-γ is shown in FIG. 11. In Table 10, the results obtained by this method for 6 assay samples are compared with the results obtained by the antiviral activity (AVA) method. Table 11 shows between-day variations for this method. The coefficient of variation was 7.4% and the results were acceptable.

TABLE 10

| | IFN titer determined by | |
|---|---|---|
| Sample No. | EIA method shown in Example 20-(ii) ($10^6$ U/l) | AVA method ($10^6$U/l) |
| 1 | 880 | 1100 |
| 2 | 880 | 1100 |
| 3 | 440 | 275 |
| 4 | 360 | 275 |
| 5 | 1060 | 1650 |
| 6 | 720 | 825 |

TABLE 11

| Date observed | IFN titer determined by EIA method shown in Example 20-(ii) |
|---|---|
| Day 0 | 6.2 |
| Day 3 | 7.2 |
| Day 7 | 6.2 |
| Day 9 | 6.0 |
| Day 15 | 5.9 |
| Day 21 | 5.9 |
| Day 30 | 6.5 |
| Average value | 6.3 |
| Coefficient of alternation | 7.4% |

The supernatant containing crude IFN-γ used in Example 13, 19 and 20 (i), (ii) was obtained by the procedure described in the following Reference Examples.

Reference Example 1

(i) Isolation of mRNA coding for human I-IFN

Lymphocytes prepared from the human peripheral blood were incubated at 37° C. in RPMI-1640 medium (containing 10% fetal calf serum) containing 15 ng/ml of 12-O-tetradecanoylphorbol-13-acetate (TPA) and 40 μg/ml of concanavalin A for I-IFN induction. After twenty-four (24) hours, the thus-induced human lymphocytes ($1 \times 10^{10}$ cells) were destructed in a thioguanidine solution (5M guanidine thiocyanate, 5% mercaptoethanol, 50 mM Tris HCl, pH 7.6, 10 mM EDTA) in a Teflon homogenizer. Then, sodium N-lauroyl sarcosinate was added in the concentration of 4% and the mixture after homogenization was layered over 6 ml of 5.7M cesium chloride [5.7M cesium chloride, 0.1M ethylenediaminetetraacetate (EDTA)] and centrifuged at 15° C. and 24000 rpm for 30 hours using a Beckman SW27 rotor to give a RNA precipitate. This RNA precipitate was dissolved in 0.25% sodium N-lauroyl sarcosinate and then precipitated with ethanol to give 8.3 mg of RNA. This RNA was allowed to be absorbed, in a high-concentration salt solution (0.5M-NaCl, 10 mM-Tris HCl; pH 7.6, 1 mM-EDTA, 0.3% SDS), on oligo (dT) cellulose and mRNA containing poly(A) was eluted with a low-concentration salt solution (10 mM-Tris HCl, pH 7.6, 1 mM EDTA, 0.3% SDS) to given 700 μg of mRNA. This mRNA was further precipitated with ethanol, then dissolved in 0.2 ml of a solution (10 mM Tris HCl, pH 7.6, 2 mM EDTA, 0.3% SDS), treated at 65° C. for 2 minutes, and fractionated by 10-35% sucrose density gradient centrifugation at 20° C. and 25,000 rpm for 21 hours using a Beckman SW27 rotor, to give 22 fractions. Aliquots of each fraction were injected into *Xenopus laevis* ooctyes and the proteins synthesized were assayed for interferon activity [antiviral activity as determined by the cytopathic effect inhibition assay using vesicular stomatitis virus on WISH cells derived from human amnion (Stewart, W. E. The interferon System, Springer N.Y., 1979, page 11)]. In this manner, it was found that fraction 12 (the sedimentation constant being 12-14S) had an activity of 195 units per μg of RNA. The mRNA in the thus-obtained fraction 12 weighed about 20 μg.

(ii) Synthesis of single-stranded RNA

Using the above mRNA and a reverse transcriptase, 100 μl of a reaction mixture (5 μg of mRNA, 50 μg of oligo (dT), 100 units of reverse transcriptase, 1 mM each of dATP, dCTP, dGTP and dTTP, 8 mM MgCl₂, 50 mM KCl, 10 mM dithiothreitol and 50 mM Tris HCl; pH 8.3) was incubated at 42° C. for 1 hour, then, deproteinized by adding phenol and treated with 0.1N NaOH at 70° C. for 20 minutes for removal of RNA by decomposition.

(iii) Synthesis of double-stranded DNA

The thus-synthesized single stranded complementary DNA was subjected to reaction in 50 μl of a reaction mixture (the same mixture as above except that the mRNA and oligo dT were absent) at 42° C. for 2 hours for synthesizing the double-stranded DNA.

(iv) Addition of dC tails

The double-stranded DNA was treated with nuclease S1 in 50 μl of a reaction mixture (double-stranded DNA, 0.1M sodium acetate, pH 4.5, 0.25M NaCl, 1.5 mM ZnSO₄, 60 units S1 nuclease) at room temperature for 30 minutes. The reaction mixture was deproteinized by adding phenol and DNA was precipitated with ethanol. The thus-obtained DNA was reacted with terminal transferase in 50 μl of a reaction mixture (double-stranded DNA, 0.14M potassium cacodylate, 0.3M Tris (base) (pH 7.6), 2 mM dithiothreitol, 1 mM CoCl₂, 0.15 mM dCTP, 30 units terminal transferase) at 37° C. for 3 minutes for elongation of the double-stranded DNA by about 20 deoxycytidine units at each 3'-end of the DNA. This series of reactions gave about 300 ng of deoxycytidine-tailed double-stranded DNA.

(v) Cleavage of *Escherichia coli* plasmid and addition of dG tails

Separately, 10 μg of *Escherichia coli* plasmid PBR 322 DNA was treated with restriction enzyme PstI in 50 μl of a reaction mixture [10 μg DNA, 50 mM NaCl, 6 mM Tris HCl (pH 7.4), 6 mM MgCl₂, 6 mM 2-mercaptoethanol, 100 μg/mg bovine serum albumin, 20 units PstI] at 37° C. for 3 hours for cleavage at the one PstI recognition site present in the pBR322DNA, the reaction mixture was then deproteinized with phenol and the DNA was further subjected to terminal transferase treatment in 50 μl of a reaction mixture [10 μg DNA, 0.14M potassium cacodylate, 0.3M Tris (base) pH 7.6, 2 mM dithiothreitol, 1 mM CoCl₂, 0.15 mM dGTP, 30 units terminal transferase at 37° C. for 3 minutes for elongation of the above pBR322 plasmid DNA by about 8 deoxyguanidines at each 3'-end thereof.

(vi) Annealing of cDNA and transformation of *Escherichia coli*

The annealing was effected by heating 0.1 μg of the thus-obtained synthetic double-stranded DNA and 0.5 μg of the above pBR322 plasmid in a solution containing 0.1M NaCl, 50 mM Tris HCl pH 7.6, 1 mM EDTA at 65° C. for 2 minutes and then at 45° C. for 2 hours, followed by gradual cooling. The transformation of *Escherichia coli* X1776 was performed by the method of Enea et al. [J. Mol. Biol., 96, 495 (1975)].

(vii) Isolation of cDNA-containing plasmid

About 8,500 tetracycline-resistant colonies were thus isolated and the DNA of each colony was fixed to a nitrocellulose filter [M. Grunstein and D.S. Hogness, Proc. Natl. Acad. Sci. USA, 72, 3961 (1975)].

Separately, based on the amino acid sequence of IFN-γ as reported by D. V. Goeddel et al. [Nature, 295, 503 (1982)], two oligonuclotides of

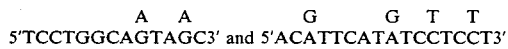

presumably corresponding to amino acids Nos. 1-5 (Cys. Try. Cys. Gln. Asp) and amino acids Nos. 77-82 (Lys. Gln. Asp. Met. Asn, Val) of said I-IFN sequence, respectively, were chemically synthesized by the triester method [R. Crea et al., Proc. Natl. Acad. Sci. USA, 75, 5765 (1978)]. These oligonucleotides were treated with T4 polynucleotide kinase in 50 μl of a reaction mixture (0.2 μg oligonucleotide, 50 mM Tris HCl pH 8.0, 10 mM MgCl₂ 10 mM mercaptoethanol, 50 μCiγ-³²P ATP, 3 units T4 polynucleotide kinase) at 37° C. for an hour. These oligopeptides thus labeled with ³²P at the 5'-end were used as probes and annealed with the DNA on the above-mentioned nitrocellulose filter by the method of Lawn et al. [Nucleic Acids Res., 9, 6103 (1981)]. Four strains were isolated by autoradiography which were reactive to the above two oligonucleotide probes.

Plasmid DNAs were isolated from the bacterial cells of each of these strains by the alkali method [H. C. Birnboim and J. Doly, Nucleic Acids Res., 7, 1513 (1979)]. The inserts in the plasmid DNAs were excised with the PstI restriction enzyme. From among the isolated plasmids, the one containing the longest insert was chosen and named "pHIT3709".

The structure (base sequence) of the cDNA sequence inserted in the pHIT3709 plasmid was then determined by the dinucleotide synthetic chain termination method and by the Maxam-Gilbert method. Said primary structure was as shown in FIG. 5.

The base sequence of the IFN-γ coding region (codon No. S1 to No. 146) of pHIT3709 was identical with that shown in FIG. 3 of Nucleic Acids Res., 10, 2487 et seq. (1982).

Reference Example 2

(i) Plasmid ptrp601 (vector being pBR322) containing the promoter portion for tryptophan synthesis in *Escherichia coli* [promotor- and operator-containing DNA fragment, 276 base pairs, G. N. bennett et al., J. Mol. Biol., 121, 113 (1978)] was constructed as the expression plasmid.

Figure 6:
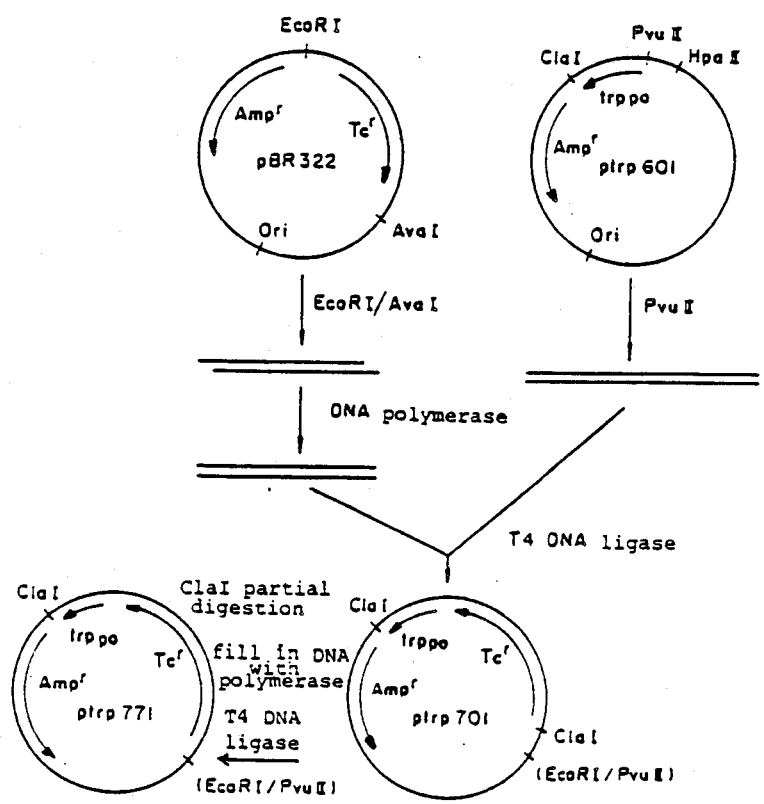
FIG. 6 shows the construction scheme for ptrp701 and ptrp771 mentioned in Reference Example 2 (i) and (ii)

Separately, plasmid pBR322 was cut with the restriction enzymes EcoRI and AvaI. The thus obtained sticky ends of EcoRI-AvaI fragment which contained tetracycline-resistant gene were filled with DNA polymerase I large fragment. This fragment was allowed to be conjugated to the PvuII cleavage site of ptrp601 using T4DNA ligase. ptrp701 was thus constructed (FIG. 6).

(ii) For the purpose of excluding either of the two restriction enzyme ClaI cleavage sites present in ptrp701, ptrp701 was subjected to partial decomposition treatment with ClaI for giving ptrp701 in which either of the two ClaI cleavage sites had been cut. After filling the sticky ends with DNA polymerase I large fragment, the thus-obtained ptrp701 was again conjugated using T4DNA ligase to give ptrp771 (FIG. 6).

(iii) pHIT3709 was cut with the restriction enzyme PstI to give the PstI fragment containing structural gene of IFN-γ. This fragment was further subjected to the partial digetion with the restriction enzyme BstNI to give the BstNi-PstI fragment which was cut at the BstNI site present in the IFN-γ structural gene. The sticky ends of the BstNI cleavage site were filled in which DNA polymerase I large fragment. The fragment thus obtained and the oligonucleotide adapter

```
CGATAATGTGTTACTGCC
TATTACACAATGACGG
```

, which was chemically synthesized by the above-mentioned triester method and contains the protein synthesis start codon ATG, were ligated using T4DNA ligase.

Figure 7:
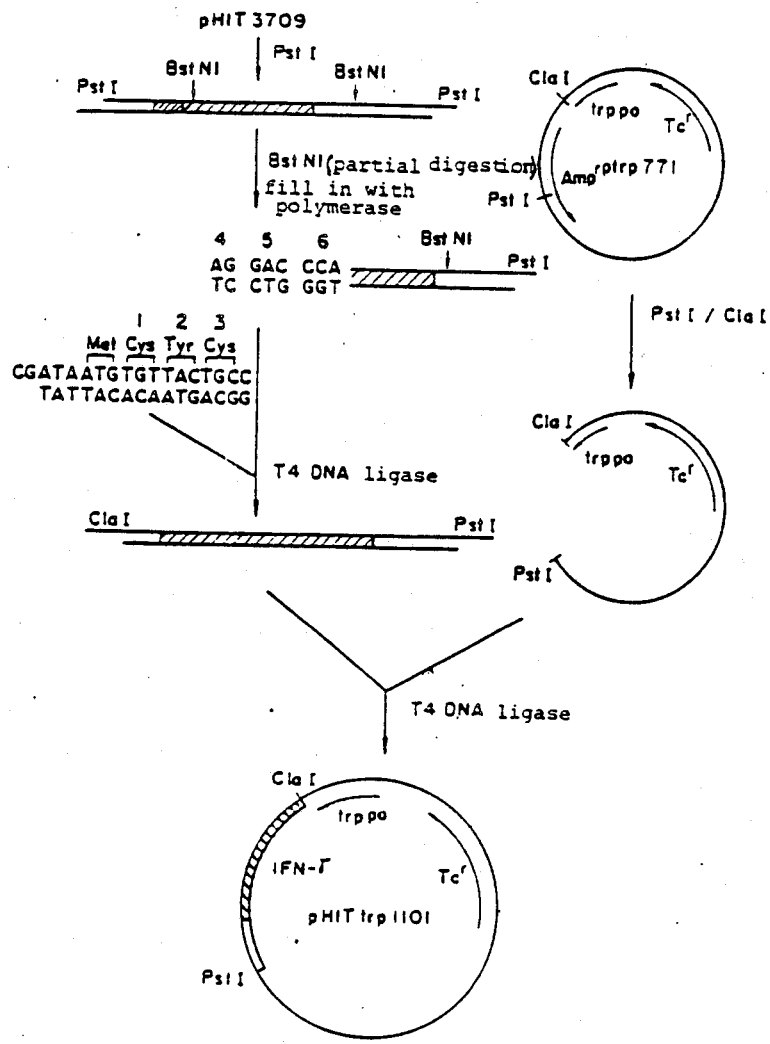
FIG. 7 shows the construction scheme for PHITtrp1101 mentioned in Reference Example 2 (iii)

Separtely, the IFN-γ gene ligated with the above-mentioned adapter was inserted into the PstI-ClaI site of Plasmid vector ptrp771 downstream from the tryptophan promoter using T4DNA ligase. An IFN-γ expression plasmid pHITtrp1101 was thus constructed (FIG. 7).

Figure 8:
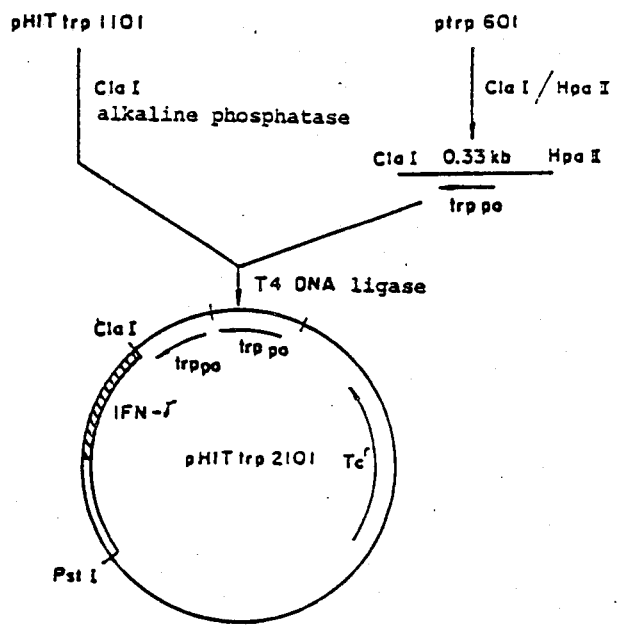
FIG. 8 shows the construction scheme for pHITtrp2101 mentioned in Reference Example 2 (iv).

(iv) pHITtrp2101 was constructed by further improvement of pHITtrp1101, as follows.

ptrp601 was first treated with the restriction enzymes ClaI and HpaII to give 0.33 Kb of the ClaI-HpaII fragment containing trp promoter. This fragment was ligated with pHITtrp1101, which was cut with ClaI and treated with alkaline phosphatase, using T4DNA ligase, pHITtrp2101 containing two successive trp promoters was thus obtained (FIG. 8).

A strain *E. coli* 294/pHIT.trp2101 was obtained by transforming *Escherichia coli* 294 (deposited as IFO-14171) with plasmid pHIT.trp2101 by the method of Cohen et al. (cit. supra).

Reference Example 3

*E. Coli* 294/pHITtrp2101 was incubated in 200 ml of M9 medium containing 8 μg/ml tetracycline, 0.4% casamino acid and 1% glucose in a 1-l flask at 37° C. When the growth of the bacteria reached KU220, 3β-indolyl acrylic acid (IAA) was added at a concentration of 30 μg/ml and the mixture was further incubated for 4 hours.

Reference Example 4

After 1.2 l of the culture solution as obtained in Reference Example 3 was centrifuged, the cells were collected and suspended in 60 ml of 0.05M Tris HCl (pH 7.6) containing 10% sucrose. To this cell suspension, 0.3 ml of 0.2M phenyl-methyl-sulfonyl fluoride (PMSF), 24 ml of 5M NaCl solution, 2.4 ml of 0.2M ethylenediamine tetraacetate (EDTA), 2.4 ml of 1M spermidine and 2.4 ml of lysozyme (5 mg/ml) were added. The mixture was allowed to stand at 0° C. for 1 hour, incubated at 37° C. for 5 minutes and, further, destructed at 0° C. for 30 seconds using a ARTEK (USA) ultrasonic disintegrator.

This lysate solution was centrifuged at 105,000× g for 1 hour and 66 ml of the supernatant were collected.

The following references, which are referred to for their disclosures at various points in this application, are incorporated herein by reference.

Nature, 256, 495 (1975)
Nature, 285, 446 (1980)
European J. of Immunology, 9, 94 (1979)
Nature, 286, 110 (1980)
The Interferon System, Springer, N.Y., 1979
Blood, 55, 711 (1980)
Blood, 56, 875 (1980)
Biochemica et Biophysica Acta, 516, 231 (1978)
Cellular Immunology, 49, 390 (1980)
Proc. Natl. Acad. Sci. USA, 79, 1820 (1982)
Nature, 295, 503 (1982)
Nucleic Acids Res., 10, 2487 (1982)
Nature, 296, 258 (1982)
The Peptides, vol. 1, Academic Press, New York, 1966
Peptide Syntheses, Maruzen, Tokyo, 1975
Experiments in Biochemistry vol 1, pages 207 to 400,
Science, 158, 1570 (1968)
Immunochemistry, 15, 429 (1971)
Eur. J. Biochem., 71, 459 (1976)
ToKyo Kagaku Dojin, 1977
Science, 144, 1334 (1964)
J. Biochemistry, 79, 223 (1976)
Immunopharmacology, 1, 3 (1978)
Current Topics in Microbiology and Immunology, 81, 1 (1978)
Applied Microbiology, 16, 1706 (1968)
J. Biological Chem., 256, 9750 (1981)
Nature, 227, 680 (1970)
Methods in Enzymology, 11, 197 (1967)
Eur. J. Biochem., 8, 189 (1969)
Altex Chromatogram, 3, 8 (1980)
J. Mol. Biol., 96, 495 (1975)
Proc. Natl. Acad. Sci. USA, 75, 5765 (1978) .
Nucleic Acids Res., 9, 6103 (1981)
Nucleic Acids Res., 7, 1513 (1979)
J. Mol. Biol., 121, 113 (1978)
What is claimed:

1. A cloned hybridoma between (a) a spleen cell of a mammal immunized with a polypeptide of the formula:

  (I)

wherein X is a bond, or a peptide or amino acid residue having 1 to 16 amino acids counting from the C terminus of the peptide chain of

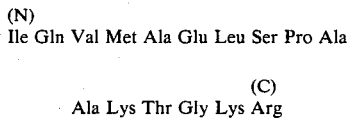

and Y is a peptide or amino acid residue having 1 to 5 amino acids counting from the N terminus of the peptide chain of

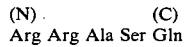

or with a conjugate between polypeptide (I) and a carrier protein and (b) lymphoid cell from a mammal of the same or different species from the immunized mammal.

2. The hybridoma of claim 1, wherein the mammal is a mouse.

3. The hybridoma of claim 1, wherein the lymphoid cell is a myeloma cell.

4. A monoclonal antibody against a polypeptide of the formula:

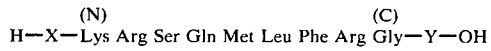

wherein X is a bond, or a peptide or amino acid residue having 1 to 16 amino acids counting from the C terminus of the peptide chain of

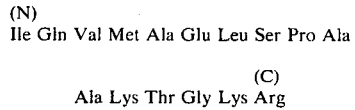

and Y is a peptide or amino acid residue having 1 to 5 amino acids counting from the N terminus of the peptide chain of

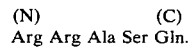

5. The monoclonal antibody of claim 4, which is capable of binding to human gamma-interferon.

6. The monoclonal antibody of claim 4, which belongs to the subclass IgG2b, when tested by the Ouchterlony method.

7. The monoclonal antibody of claim 4, which belongs to the subclass IgG1, when tested by the Ouchterlony method.

8. Monoclonal antibodies to human gamma-interferon protein, produced by hybridoma cell line ATCC HB8699 or ATCC HB8700.

9. A hybridoma cell which produces a monoclonal antibody to human gamma-interferon, the cell being from the hybridoma cell line ATCC HB8699 or the hybridoma cell line ATCC HB8700.

* * * * *